(12) United States Patent
Didyk et al.

(10) Patent No.: US 11,957,394 B2
(45) Date of Patent: Apr. 16, 2024

(54) SCREW CADDY

(71) Applicant: J.M. Longyear Manufacturing, LLC, Marquette, MI (US)

(72) Inventors: Peter J. Didyk, Northville, MI (US); Joseph Mohar, Marquette, MI (US); Tyler Losinski, Negaunee, MI (US); Craig Wiseman, Marquette, MI (US); Erik Alanko, Marquette, MI (US)

(73) Assignee: J.M. LONGYEAR MANUFACTURING, LLC, Marquette, MI (US)

( * ) Notice: Subject to any disclaimer, the term of this patent is extended or adjusted under 35 U.S.C. 154(b) by 123 days.

(21) Appl. No.: 17/114,566

(22) Filed: Dec. 8, 2020

(65) Prior Publication Data

US 2021/0267651 A1  Sep. 2, 2021

Related U.S. Application Data

(63) Continuation-in-part of application No. 16/802,713, filed on Feb. 27, 2020, now abandoned.

(51) Int. Cl.
| | | |
|---|---|---|
| *A61B 17/90* | (2006.01) |
| *A61B 17/80* | (2006.01) |
| *A61B 17/86* | (2006.01) |
| *A61B 17/88* | (2006.01) |
| *A61B 17/00* | (2006.01) |

(52) U.S. Cl.
CPC .......... *A61B 17/865* (2013.01); *A61B 17/808* (2013.01); *A61B 17/8894* (2013.01); *A61B 2017/00862* (2013.01)

(58) Field of Classification Search
CPC . A61B 17/8894; A61B 17/808; A61B 17/865; A61B 17/1728; A61B 17/8875; A61B 17/90
See application file for complete search history.

(56) References Cited

U.S. PATENT DOCUMENTS

| | | |
|---|---|---|
| 5,192,293 A | 3/1993 | Cartwright et al. |
| 5,766,221 A | 6/1998 | Benderev et al. |
| 7,052,499 B2 | 5/2006 | Steger et al. |
| 7,153,309 B2 | 12/2006 | Huebner et al. |

(Continued)

FOREIGN PATENT DOCUMENTS

| | | |
|---|---|---|
| EP | 1488753 | 12/2004 |
| EP | 1429675 B1 | 10/2007 |

(Continued)

OTHER PUBLICATIONS

Creative Mechanisms, "Everything you need to know about Nylon", https://www.creativemechanisms.com/blog/3d-printing-injection-molding-cnc-nylon-plastic-pa#:~:text=Nylon%20is%20classified%20as%20a,in%20the%20case%20of%20Nylon, p. 2 of provided .pdf file. (Year: 2022).*

(Continued)

*Primary Examiner* — Amy R Sipp
(74) *Attorney, Agent, or Firm* — Kagan Binder, PLLC

(57) ABSTRACT

A fastener caddy for use with a bone plate. The fastener caddy includes preloaded fasteners that are positioned above the fastener apertures in the bone plate once the caddy is coupled to the bone plate. The caddy permits the driving of fasteners with the fastener already in proper alignment and without the need to retrieve each individual fastener. Once the fasteners are installed into the bone plate.

23 Claims, 32 Drawing Sheets

(56) References Cited

U.S. PATENT DOCUMENTS

| | | | |
|---|---|---|---|
| 7,776,047 | B2 | 8/2010 | Fanger et al. |
| 7,833,226 | B2 | 11/2010 | Grabowski et al. |
| 8,162,138 | B2 | 4/2012 | Bettenhausen et al. |
| 8,292,898 | B2 | 10/2012 | Castaneda et al. |
| 8,486,114 | B2 | 7/2013 | Gillard et al. |
| 8,632,574 | B2 | 1/2014 | Kortenbach et al. |
| 8,685,068 | B2 | 4/2014 | Sixto et al. |
| 8,789,713 | B2 | 7/2014 | Koller |
| 8,992,583 | B2 | 3/2015 | Bottlang et al. |
| 9,107,712 | B2 | 8/2015 | Castaneda et al. |
| 9,138,244 | B2 | 9/2015 | Mebarak et al. |
| 9,358,054 | B2 | 6/2016 | Garcia et al. |
| 9,474,558 | B2 | 10/2016 | Sixto, Jr. et al. |
| 9,480,512 | B2 | 11/2016 | Orbay |
| 9,492,213 | B2 | 11/2016 | Orbay |
| 9,510,879 | B2 | 12/2016 | Bottlang et al. |
| 9,642,656 | B2 | 5/2017 | Kotuljac et al. |
| 9,788,878 | B2 | 10/2017 | Garcia et al. |
| 9,801,672 | B2 | 10/2017 | Garcia et al. |
| 9,820,755 | B2 | 11/2017 | Garcia et al. |
| 10,226,290 | B2 | 3/2019 | Steffensmeier et al. |
| 10,307,193 | B2 | 6/2019 | Garcia et al. |
| 10,426,531 | B2 | 10/2019 | Pech et al. |
| 10,517,659 | B2 | 12/2019 | Sixto et al. |
| 10,639,084 | B2 | 5/2020 | Garcia et al. |
| 10,675,074 | B2 | 6/2020 | Roby et al. |
| 10,758,290 | B2 | 9/2020 | Detweiler et al. |
| 10,905,443 | B2 | 2/2021 | Whitaker et al. |
| 10,918,430 | B2 | 2/2021 | Bottlang et al. |
| 10,939,927 | B2 | 3/2021 | Garcia et al. |
| 10,952,756 | B2 | 3/2021 | Garcia et al. |
| 11,439,447 | B2 | 9/2022 | Detweiler et al. |
| 2004/0204710 | A1 | 10/2004 | Patel et al. |
| 2010/0069969 | A1 | 3/2010 | Ampuero et al. |
| 2010/0094294 | A1 | 4/2010 | Gillard et al. |
| 2010/0179600 | A1 | 7/2010 | Steger et al. |
| 2011/0004254 | A1* | 1/2011 | Beger ............... A61B 17/1728 606/289 |
| 2011/0264152 | A1 | 10/2011 | Weiman et al. |
| 2012/0136392 | A1 | 5/2012 | Keegan et al. |
| 2012/0138495 | A1 | 6/2012 | Bettenhausen et al. |
| 2014/0309702 | A1 | 10/2014 | Wand |
| 2015/0038969 | A1 | 2/2015 | Garcia et al. |
| 2015/0119887 | A1 | 4/2015 | May et al. |
| 2015/0124990 | A1 | 5/2015 | Wirth et al. |
| 2015/0230845 | A1 | 8/2015 | Jensen |
| 2016/0051297 | A1 | 2/2016 | Steffensmeier et al. |
| 2016/0058564 | A1 | 3/2016 | Zappacosta et al. |
| 2018/0177510 | A1 | 6/2018 | Whitaker et al. |
| 2019/0046251 | A1 | 2/2019 | Detweiler et al. |
| 2019/0090925 | A1 | 3/2019 | Detweiler et al. |
| 2019/0150997 | A1 | 5/2019 | Sixto et al. |
| 2019/0167320 | A1 | 6/2019 | Steffensmeier et al. |
| 2019/0380755 | A1* | 12/2019 | Tsai ..................... A61B 17/808 |
| 2020/0337751 | A1 | 10/2020 | Detweiler et al. |
| 2020/0352617 | A1 | 11/2020 | Detweiler et al. |
| 2021/0153913 | A1 | 5/2021 | Walsh et al. |
| 2022/0047309 | A1 | 2/2022 | May et al. |
| 2022/0125492 | A1 | 4/2022 | Steffensmeier et al. |
| 2022/0257293 | A1 | 8/2022 | May et al. |
| 2022/0354551 | A1 | 11/2022 | Detweiler et al. |

FOREIGN PATENT DOCUMENTS

| | | | |
|---|---|---|---|
| EP | 2922484 B1 | 9/2015 | |
| EP | 2939790 A1 * | 11/2015 | ........... B25B 23/005 |
| EP | 2939790 A1 | 11/2015 | |
| EP | 3182905 A1 | 6/2017 | |
| EP | 2623059 B1 | 6/2018 | |
| EP | 3363394 A2 | 8/2018 | |
| EP | 3033018 B1 | 10/2019 | |
| EP | 3740146 A1 | 11/2020 | |
| WO | 2006124188 | 11/2006 | |
| WO | 2014144479 A1 | 9/2014 | |
| WO | 2019/143690 A1 | 7/2019 | |
| WO | 2019143690 A1 | 7/2019 | |

OTHER PUBLICATIONS

Mall, "Clinical morphology of the sternum," https://pubmed.ncbi.nlm.nih.gov/1768775/#:~:text=Width%20and%20thickness%20maxima%20(7.4,respectively)%20show%20relatively%20minor%20differences. (Year: 2023).*

PCT/US21/19824, Notification of Transmittal of the International Search Report and the Written Opinion of the International Search Authority, dated May 4, 2021, 15 pgs.

PCT/US21/19842, Notification of Transmittal of the International Search Report and the Written Opinion of the International Search Authority, dated May 6, 2021, 19 pgs.

Franco et al., "Use of steel bands in sternotomy closure: implications in high-risk cardiac surgical population" Interactive CardioVascular and Thoracic Surgery 8 (2009) 200-205.

Glennie et al., "Strength of wired sternotomy closures: effect of number of wire twists" Interactive Cardiovascular and Thoracic Surgery 2 (2003) 3-5.

Virage OCT Spinal Fixation System—Surgical Technique Guide, Zimmer Biomet Spine, Inc., 56 pages, 2018.

Thoracolumbar Solutions Timberline MPF Lateral Modular Plate Fixation System—Surgical Techique Guide, Zimmer Biomet Spine, Inc., 44 pages, 2018.

Orthofix Connector System—a Comprehensive Solution, Orthofix Holdings, Inc. 6 pages, May 2020.

* cited by examiner

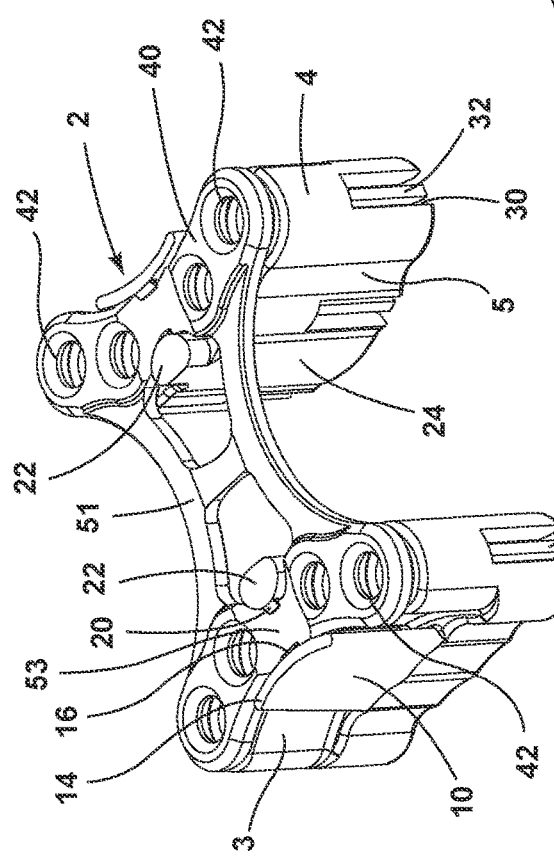

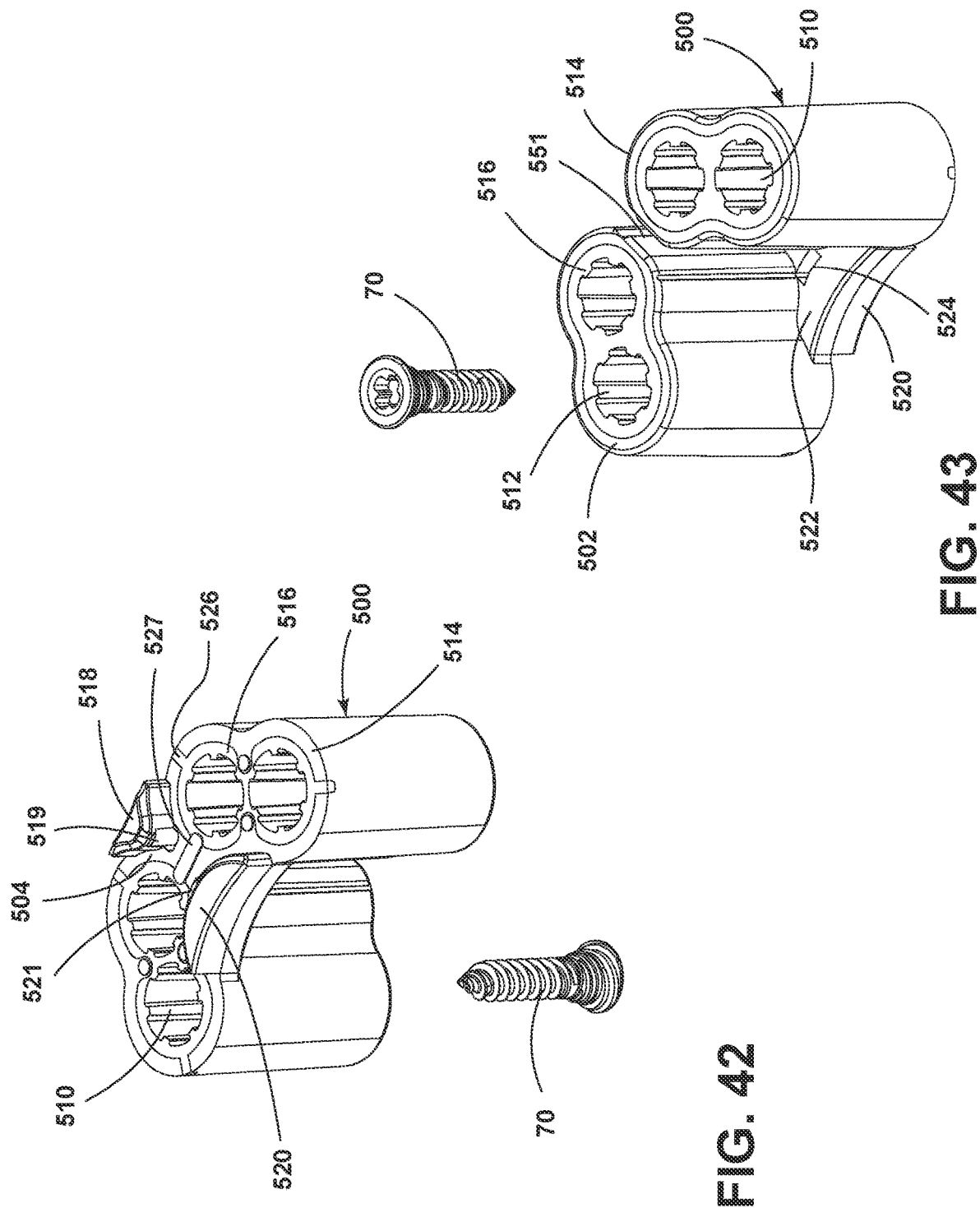

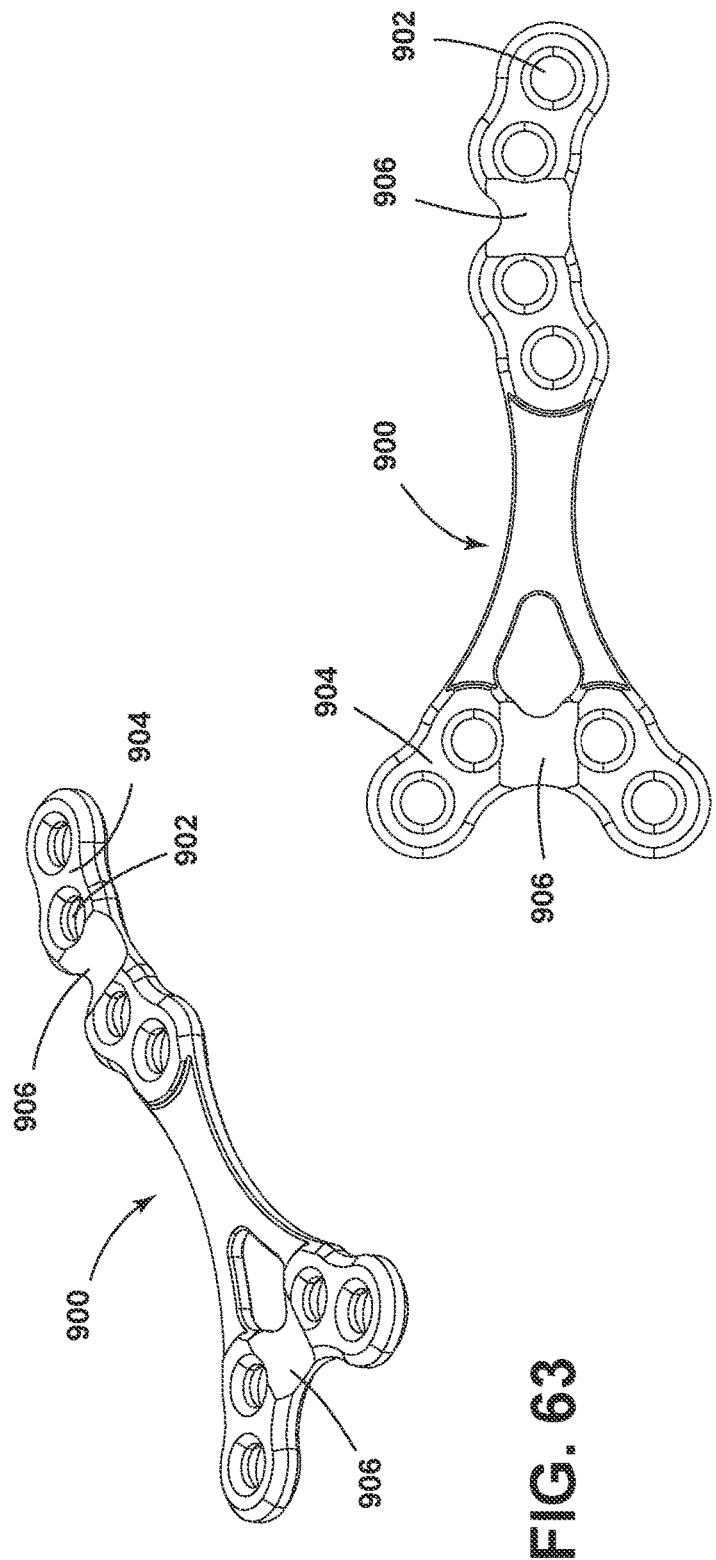
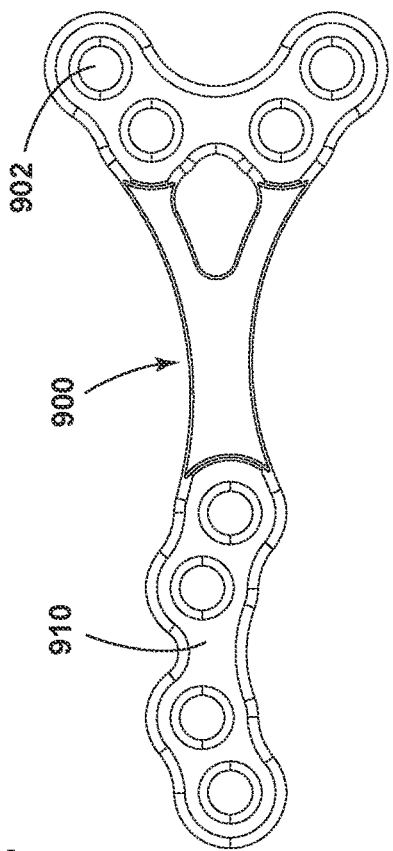
FIG. 63
FIG. 64
FIG. 65

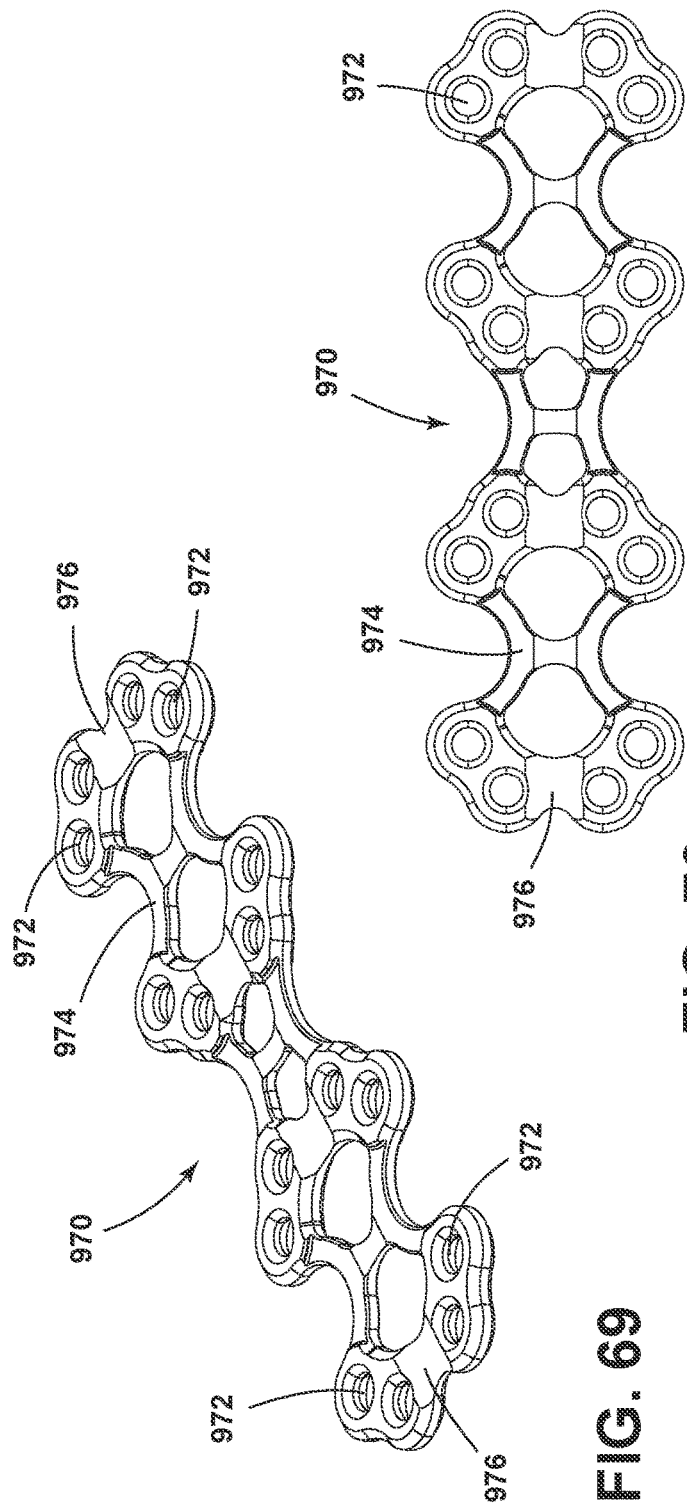
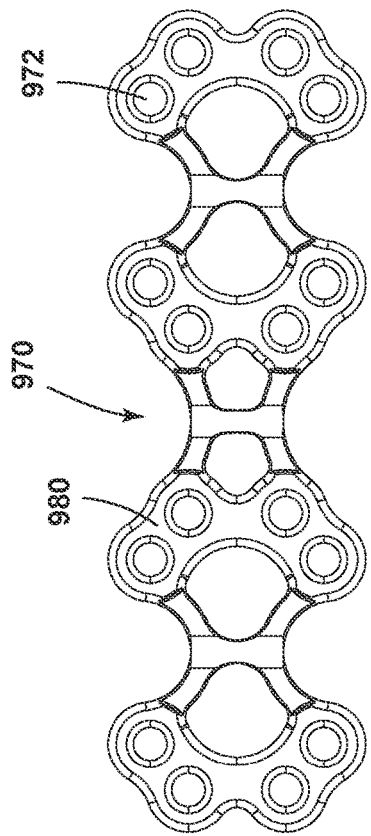
FIG. 69
FIG. 70
FIG. 71

SCREW CADDY

CLAIM OF PRIORITY

The present application is a continuation-in-part of commonly assigned U.S. patent application Ser. No. 16/802,713, filed Feb. 27, 2020, entitled SCREW CADDY, the entirety of which is incorporated herein by reference.

BACKGROUND OF THE INVENTION

The present invention generally relates to surgical equipment and, more particularly, to surgical instruments used to fix or locate segments of bone.

Bone plates and surgical fasteners, such as screws, are used for the fixation of bone during surgery. A standard bone plate is a piece of material, usually metal, having circular and/or slotted holes through which bone screws are fixated. Typically, the bone plate is used to span a discontinuity between two adjacent bones or bone segments, and the screws are placed through holes in the bone plate that are positioned on both sides of the fracture to secure the plate to the bone segments to promote fusion between the adjacent bone or bone segments.

The length, shape, contour, and segments of a bone plate can vary, depending upon where the bone plate is inserted. For example, some bone plates could have multiple segments, while others could have a single segment. Moreover, multiple segment bone plates can include spaced apart segments.

Typically once the bone plate and fasteners (anchors) are sterilized, the surgeon will locate the bone plate on the bone and then insert each individual fastener, one at a time. This requires another person to provide the screws to the surgeon and/or the surgeon to retrieve a screw from a screw rack. This is a time-consuming process. Moreover, the surgeon will need to locate each individual screw over each individual hole in the bone plate. Again, this takes additional time and can also result in screws becoming cross-threaded and/or being advanced too far or not far enough into the bone.

Accordingly, the need exists for a surgical device that pre-locates the screws over the holes in the bone plate and permits the screws to be easily advanced by use of a driving tool, while maintaining the screws in the proper alignment and preventing over-tightening of the screws.

SUMMARY OF THE INVENTION

One aspect of the present invention is a surgical plate and caddy assembly. The assembly includes a bone plate having a top surface, a bottom surface with at least one indented section, and a plurality of fastener apertures. The surgical plate and caddy assembly also includes a caddy that is coupled to the bone plate. The caddy has a top surface, a bottom surface, and at least two side surfaces. The caddy also has a plurality of fastener apertures that are aligned with the plurality of fastener apertures in the bone plate when the caddy is coupled to the bone plate. At least two of the caddy side surfaces include a clip portion that has a tab that extends below and contacts the indented surface on the bottom surface of the bone plate. At least one of the clip portions will deflect to remove the tab from contact with the indented surface of the bone plate when the caddy is flexed. The surgical plate and caddy assembly also includes a plurality of fasteners that are inserted into the plurality of fastener apertures in the caddy.

Another aspect of the present invention is a method of installing fasteners into the bone plate. The method includes forming a caddy that has a top surface, a bottom surface, and at least two clip portions. The caddy also has a plurality of fastener apertures with internal ribs. The method includes inserting fasteners into the fastener apertures in the caddy. The caddy is then coupled to a bone plate such that the fastener and the fastener apertures of the caddy are aligned with the fastener apertures in the bone plate. When the caddy is coupled to the bone plate, the clip portions are engaged to a lower surface of the bone plate. The method includes advancing the fasteners to secure the bone plate to the bone. The method includes removing the caddy from the bone plate by flexing the caddy to deflect at least one of the clip portions.

Yet another aspect of the present invention is a surgical fastener caddy guide. The caddy guide includes a caddy body that has a top surface, a bottom surface, and at least two side surfaces. The caddy body also has at least one fastener aperture with internal ribs extending through the caddy body from the top surface of the caddy body to the bottom surface of the caddy body. One side surface of the caddy body includes a first clip member with a tab on the lower surface of the first clip member.

BRIEF DESCRIPTION OF THE DRAWINGS

Examples of the preferred embodiments are shown in the drawings. It should be appreciated, however, that the invention is not limited to the precise arrangements and instrumentally shown. In the drawings:

FIG. 1 is a bottom perspective view of two fastener caddies coupled to a bone plate;

FIG. 2 is a top perspective view of the bone plate and caddy assembly shown in FIG. 1;

FIG. 42 is a bottom perspective view of another embodiment of a fastener caddy;

FIG. 43 is a top perspective view of the fastener caddy shown in FIG. 42;

FIG. 63 is a front perspective view of another embodiment of a bone plate;

FIG. 64 is a bottom view of the bone plate shown in FIG. 63;

FIG. 65 is a top view of the bone plate shown in FIG. 63;

FIG. 69 is a front perspective view of another embodiment of a bone plate;

FIG. 70 is a bottom view of the bone plate shown in FIG. 69;

FIG. 71 is a top view of the bone plate shown in FIG. 69;

DETAILED DESCRIPTION

Figures 74, 75:
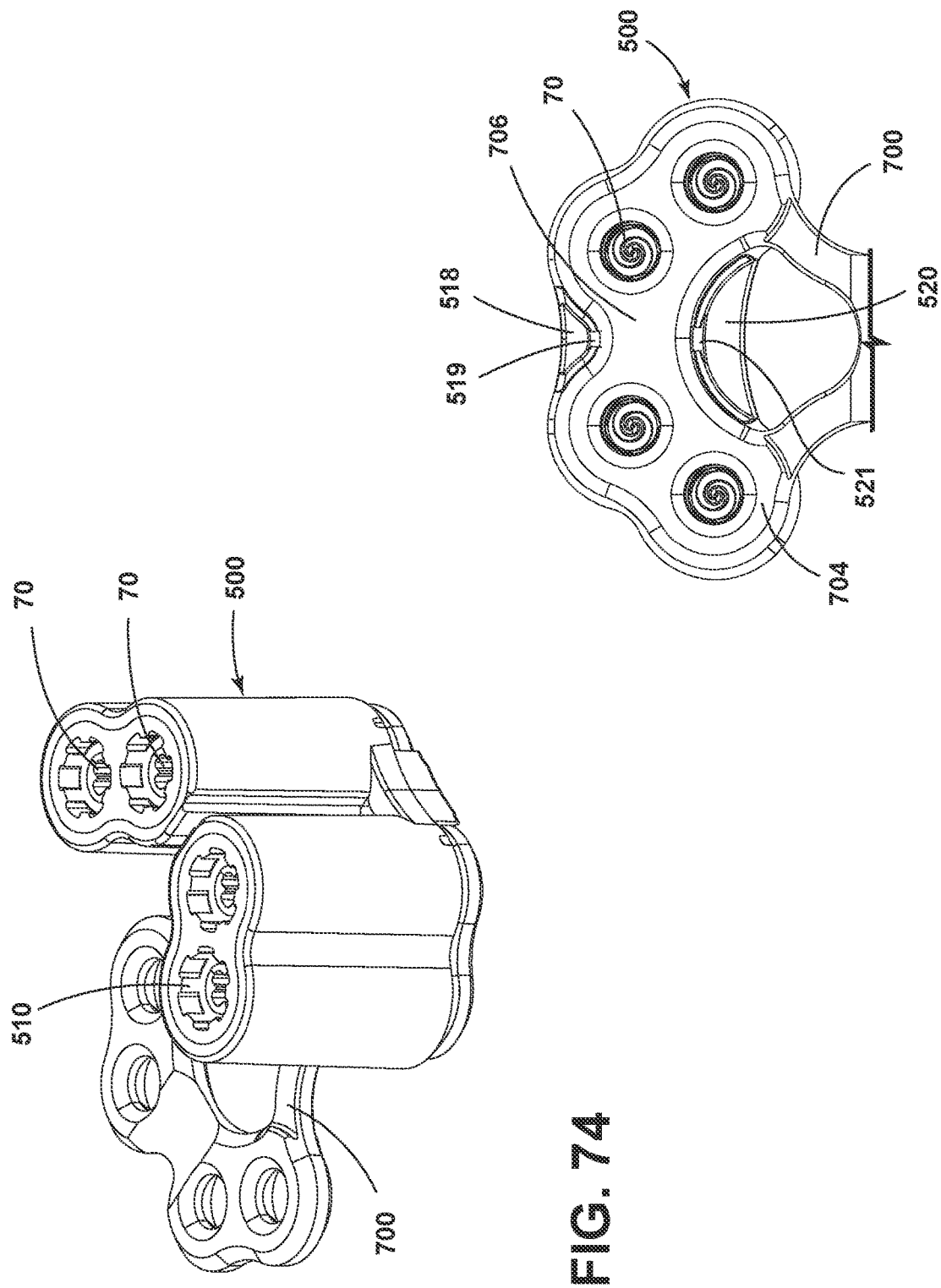
FIG. 74 is a front perspective view of the fastener caddy shown in FIG. 42 coupled to the bone plate shown in FIG. 54.
FIG. 75 is a partial bottom view of the assembly shown in FIG. 74.

For purposes of description herein, the terms "upper," "lower," "right," "left," "rear," "front," "vertical," "horizontal," and derivatives thereof shall relate to the invention as oriented in FIGS. 1-75. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 9:
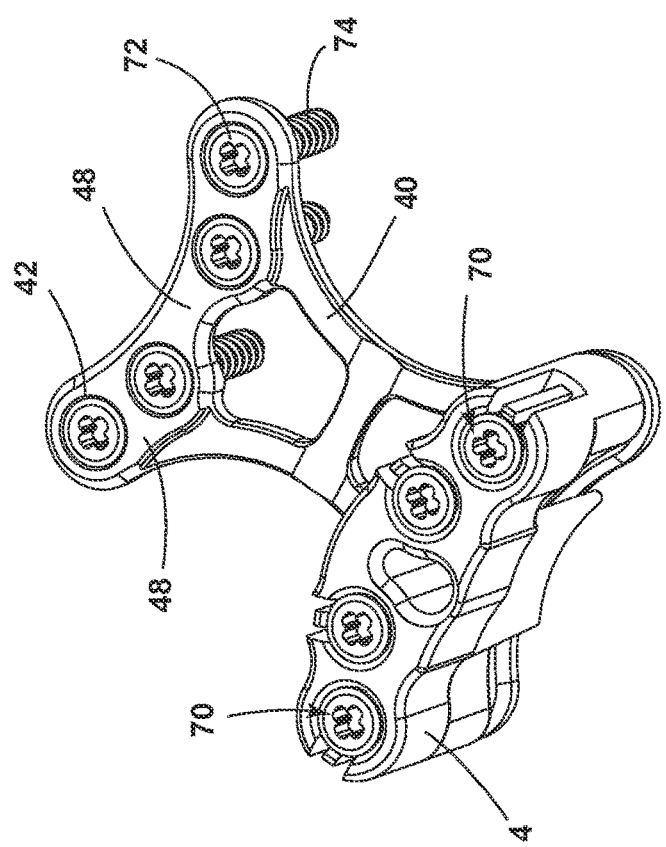
FIG. 9 is a top perspective view of the bone plate and caddy assembly shown in FIG. 2 with one of the two fastener caddies removed.
Figure 12:
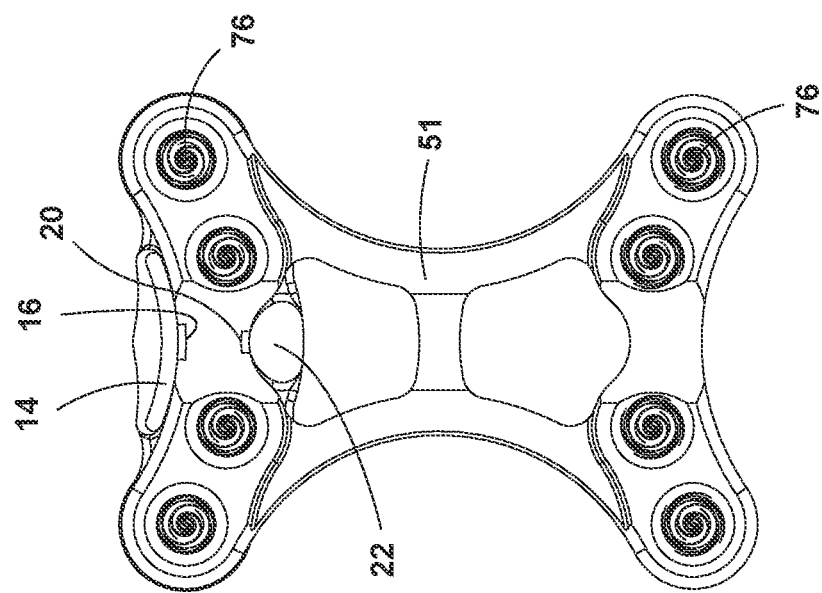
FIG. 12 is a bottom view of the bone plate and caddy assembly shown in FIG. 9.
Figure 11:
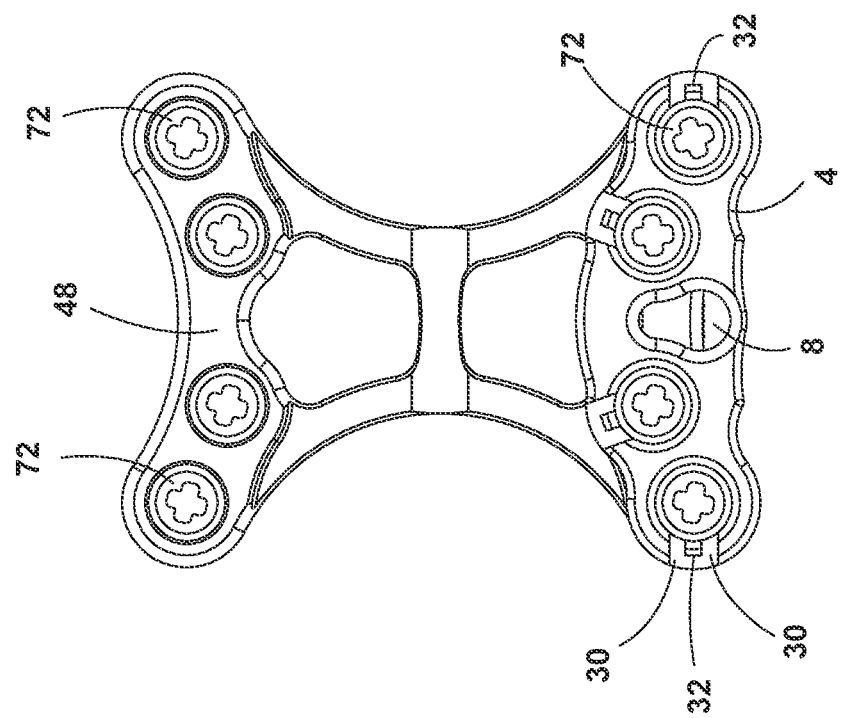
FIG. 11 is a top view of the bone plate and caddy assembly shown in FIG. 9.

FIGS. 1-4 and 9-12 illustrate one embodiment of a fastener caddy assembly 2 that is useful for understanding the inventive concepts disclosed herein. The fastener caddy assembly 2 includes a fastener caddy 4 that is coupled to a first side 44 of a bone plate 40 and a fastener caddy 4 coupled to a second side 46 of the bone plate 40. A number of fasteners 70 are preloaded into the fastener caddies 4, as illustrated in FIG. 9, and each fastener caddy 4 can be removed from the bone plate 40 once the fasteners 70 have been installed into the bone plate 40.

The fastener caddy 4 has a top surface 13 and a bottom surface 12. Fastener caddy 4 also has sides 3 and 5 that have the same general contour as the segment of the bone plate 40 to which it is coupled. The fastener caddy 4 also has a number of fastener apertures 6. The fastener apertures 6 can be unthreaded, partially threaded, or entirely threaded. In the illustrated embodiments, the fastener caddy 4 has four fastener apertures 6, although any number of fastener apertures can be used depending upon the size and purpose of the associated bone plate 40. The top surface of the fastener aperture 6 includes a tapered portion 7. The tapered portion 7 will generally engage a surface of the head 72 of a fastener 70 when the fasteners are preloaded into the fastener caddy 4. The fastener caddy 4 also has an insertion tool aperture 8 with a similarly tapered surface 9.

Figure 4:
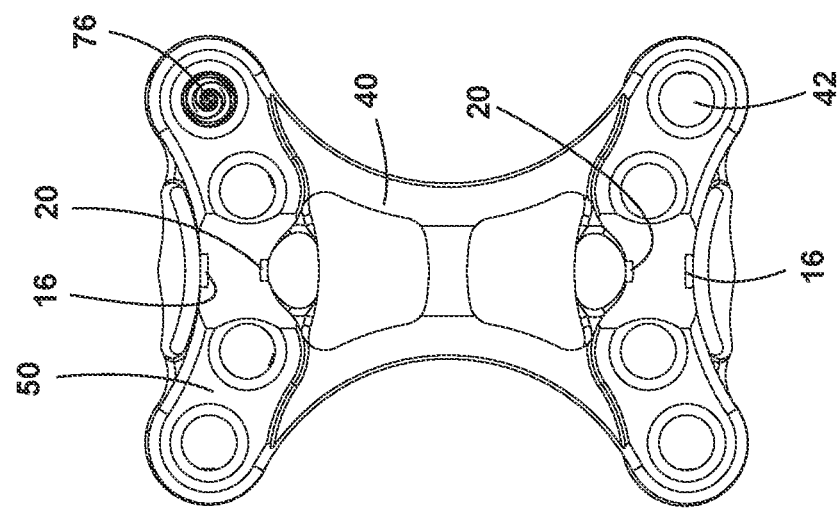
FIG. 4 is a bottom view of the bone plate and caddy assembly shown in FIG. 3.
Figure 3:
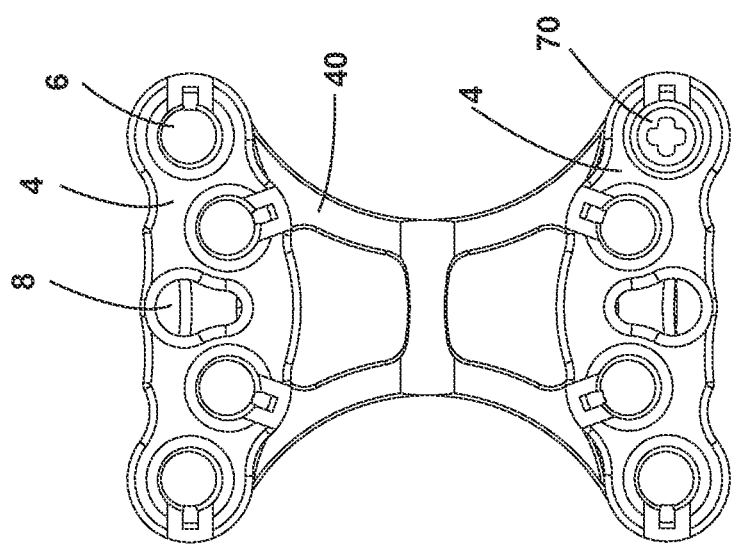
FIG. 3 is a top view of the bone plate and caddy assembly shown in FIG. 1 with a single fastener.
Figure 7:
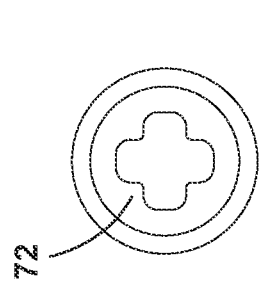
FIG. 7 is a top view of a fastener.
Figure 8:
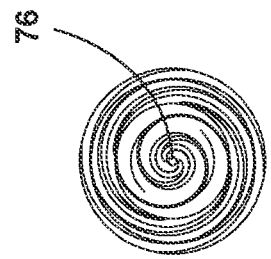
FIG. 8 is a bottom view of a fastener.
Figure 6:
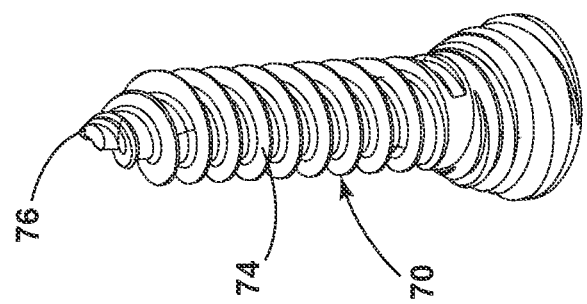
FIG. 6 is a side perspective view of a fastener.
Figure 5:
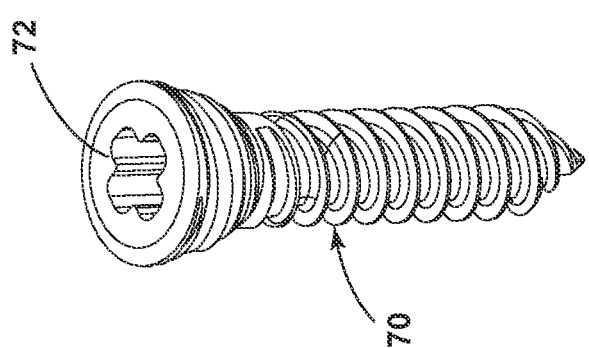
FIG. 5 is a front perspective view of a fastener.
Figure 10:
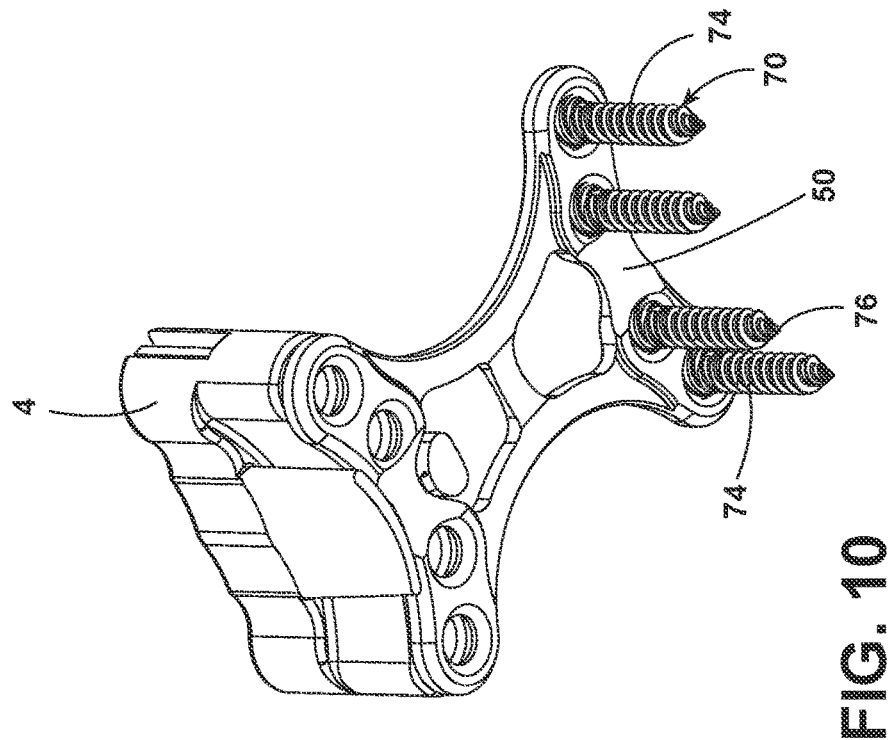
FIG. 10 is a bottom perspective view of the bone plate and caddy assembly shown in FIG. 9.

The fastener caddy 4 couples to the bone plate 40 by the engagement of tabs 16 and 20. Specifically, the fastener caddy 4 has a first clip 10 on side 3 with a lower surface 14 and a tab 16 extending therefrom. The opposite side 5 of the fastener caddy 4 has a second clip 24 with a bottom surface 22 and a tab 20. As illustrated in FIGS. 1 and 4, the tabs 16, 20 engage the bottom surface 50 of bone plate 40.

As illustrated in FIGS. 1-4, bone plate 40 has a number of fastener apertures 42 that extend from the top surface 48 to the bottom surface 50 of the bone plate 40. The bone plate 40, illustrated in FIGS. 1-4 and 9-12, has a first side 44 and a second side 46. The first side 44 is on the side 3 of fastener caddy 4, while the side 46 is on the side 5 of fastener caddy 4. The bone plate 40 illustrated in FIGS. 1-4 and 9-12 has two segments that are connected by a middle portion 51. Thus, the bone plate 40 has two segments that are spaced apart, which each segment having the first side 44 and the second side 46. As illustrated in these Figures, the fastener apertures 6 of fastener caddy 4 are in alignment with the fastener apertures 42 of bone plate 40 when fastener caddy 4 is coupled to the bone plate 40. As illustrated in FIG. 9, this permits the fasteners 70 to be preloaded into the fastener caddy 4 and situated above the fastener apertures 42 and bone plate 40 before the fasteners 70 are driven by the surgeon.

FIG. 9 illustrates one side of the bone plate 40 having the fasteners 70 already installed into the fastener aperture 42 of the bone plate 40, while the other side still has the fastener caddy 4 with the preloaded fasteners 70. The fastener caddy 4 is removed once the fasteners 70 have been installed into the bone plate 40 by the insertion of an insertion tool into insertion tool aperture 8. The tool has a section that presses one or both of the clip portions 10, 24 of the fastener caddy 4 to disengage the one or both of the tab members 16, 20 from the bottom surface 50 from the bone plate 40 thereby permitting the decoupling and removal of the fastener caddy 4 from bone plate 40.

The embodiment of the fastener caddy 4 illustrated in FIGS. 1-4 and 9-12 has at least one finger 32 located on each of the fastener apertures 6. The finger 32 is formed in a side wall of the fastener aperture 6 in between two vertical slots 30. The finger 32 includes tapered surface 34 that generally matches the tapered surface 7 of the fastener aperture 6. The finger 32 also includes a groove 36 located below the tapered surface 34 that is located between the tapered surface 34 and an extension 37. The groove 36 interfaces with one or more threads on the threaded shank 74 of the fastener 70, preventing the fastener 70 from falling out of the fastener aperture 6 in fastener caddy 4. The interface between the groove 36 and the threaded shank 74 allows for a variation in the length and diameter of the fastener 70 that is inserted into the fastener aperture 6 in fastener caddy 4. The shape of the groove 36 can match the thread pitch of the threaded shank 74 and lock the fastener 70 in place in the fastener aperture 6. When the pre-installed fasteners 70 are advanced toward the bone plate 40, the fingers 32 will flex and permit the fasteners 70 to be advanced toward and installed into the bone plate 40. While the illustrated embodiment, in FIGS. 1-4 and 9-12, show a single finger 32 with each aperture 6, multiple fingers 32 can be used with any given fastener aperture 6.

As illustrated in FIGS. 5-8, fastener 70 includes a head 72 with a shaped surface for being advanced by a driving bit. In the illustrated embodiments, the head 72 receives a Phillips driving bit. The threaded shank 74 of the fastener 70 terminates in a lower tip 76.

Figure 14:
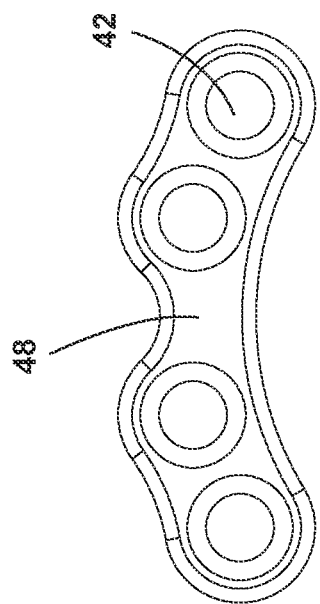
FIG. 14 is a top view of the bone plate shown in FIG. 13.
Figure 15:
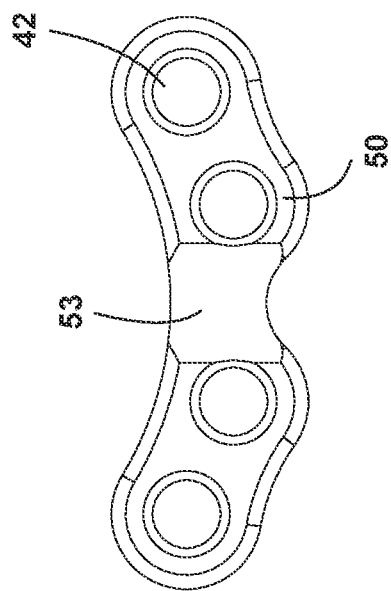
FIG. 15 is a bottom view of the bone plate shown in FIG. 13.
Figure 13:
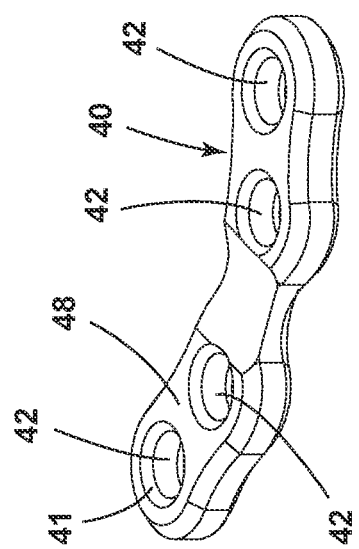
FIG. 13 is a front perspective view of another embodiment of a bone plate.

While FIGS. 1-4 and 9-12 illustrate a bone plate 40 with two segments that are connected by middle portion 51, FIGS. 13-15 illustrate another embodiment of a bone plate 40 having a single segment. Again, the bone plate 40 has fastener apertures 42 with a tapered surface 41 that will engage a portion of the head 72 of fastener 70 when the fasteners are fully installed into the bone plate 40. The bone plate 40 also has a top surface 48 and a bottom surface 50.

Figure 17:
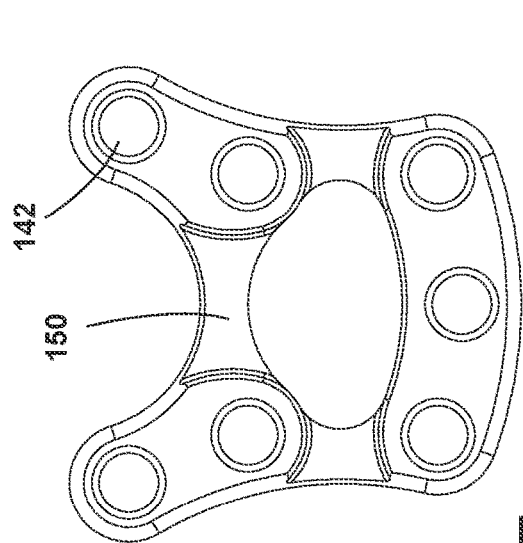
FIG. 17 is a bottom view of the bone plate shown in FIG. 16.
Figure 18:
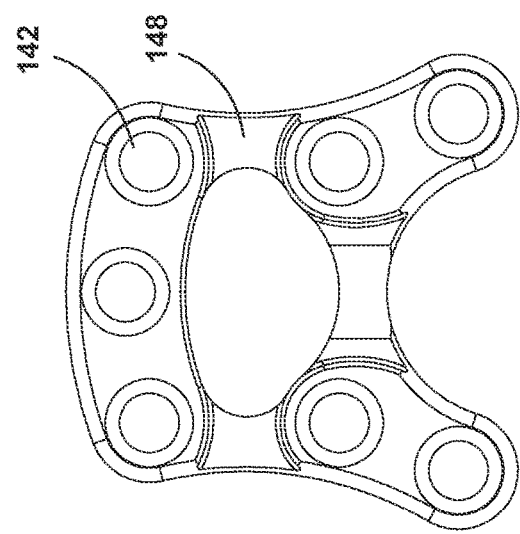
FIG. 18 is a top view of the bone plate shown in FIG. 16.
Figure 16:
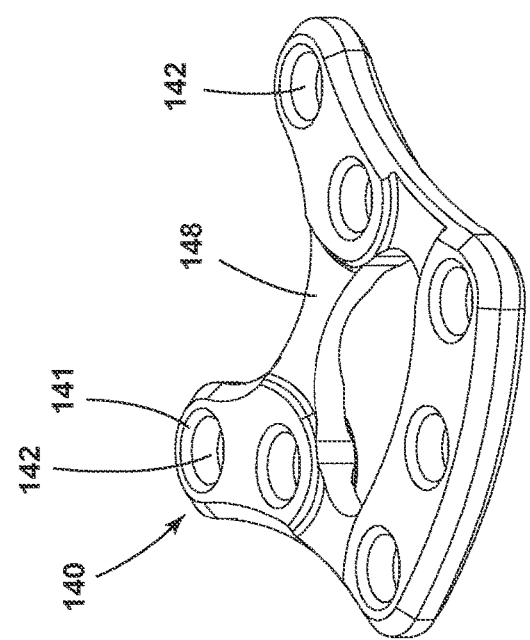
FIG. 16 is a front perspective view of another embodiment of a bone plate.
Figure 19:
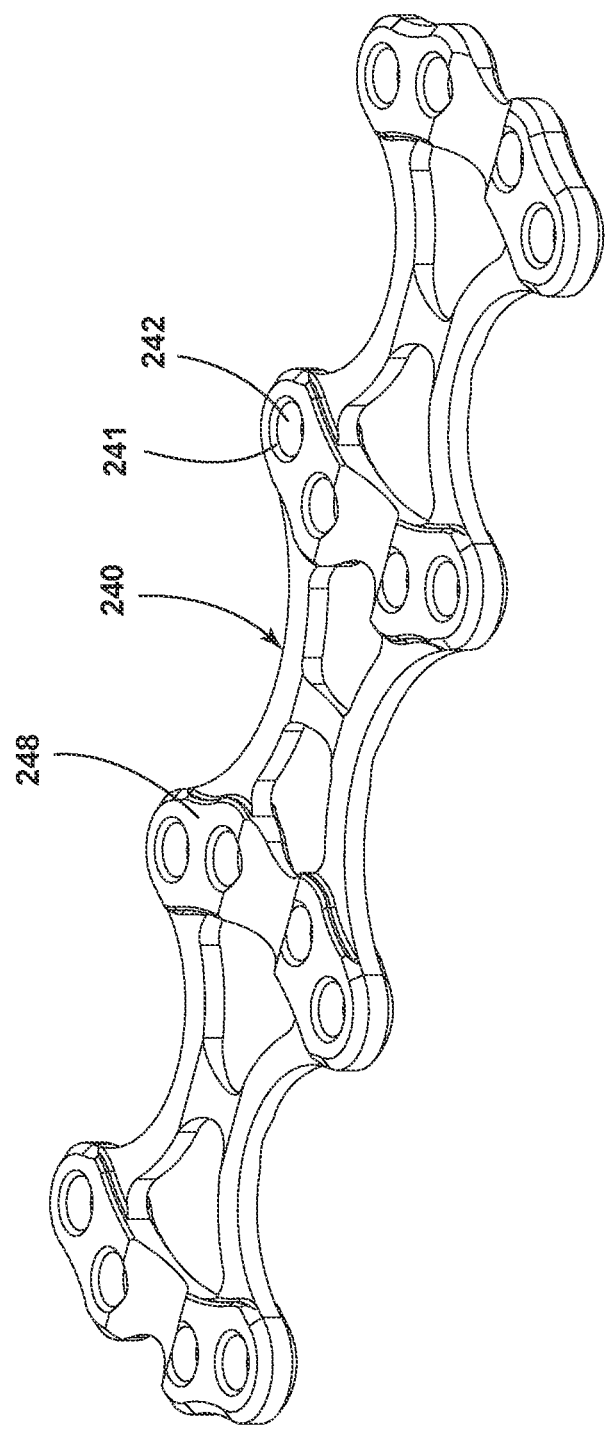
FIG. 19 is a front perspective view of another embodiment of the bone plate.
Figure 20:
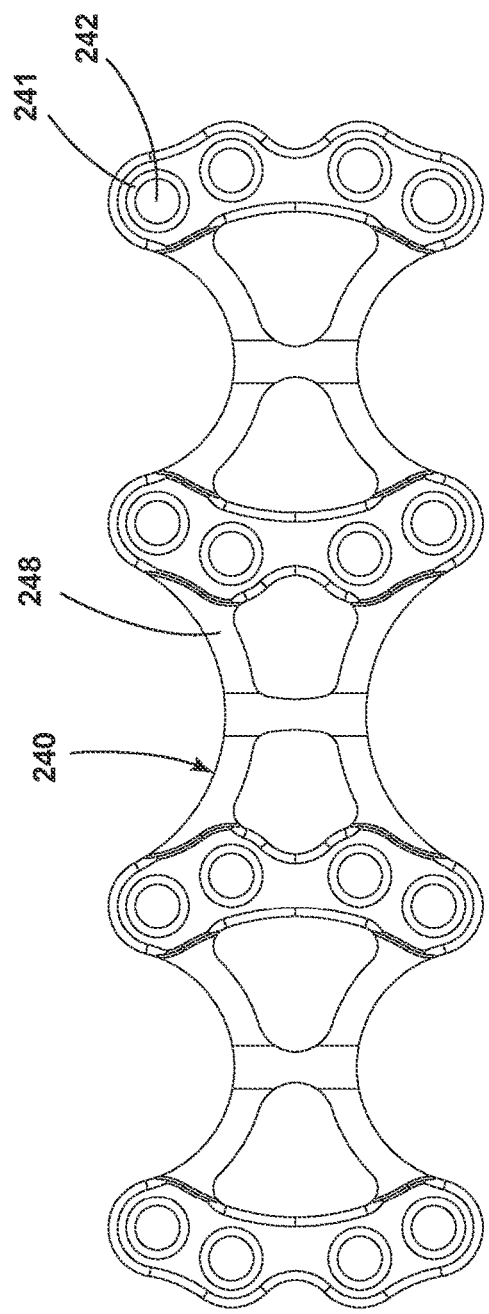
FIG. 20 is a top view of the bone plate shown in FIG. 19.
Figure 21:
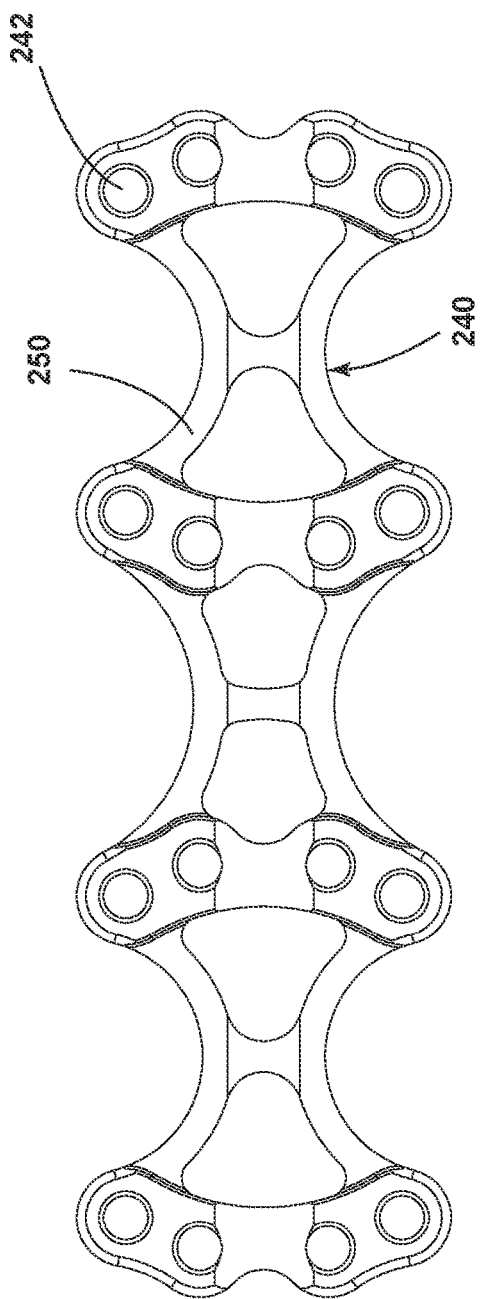
FIG. 21 is a bottom view of the bone plate shown in FIG. 19.
Figure 22:
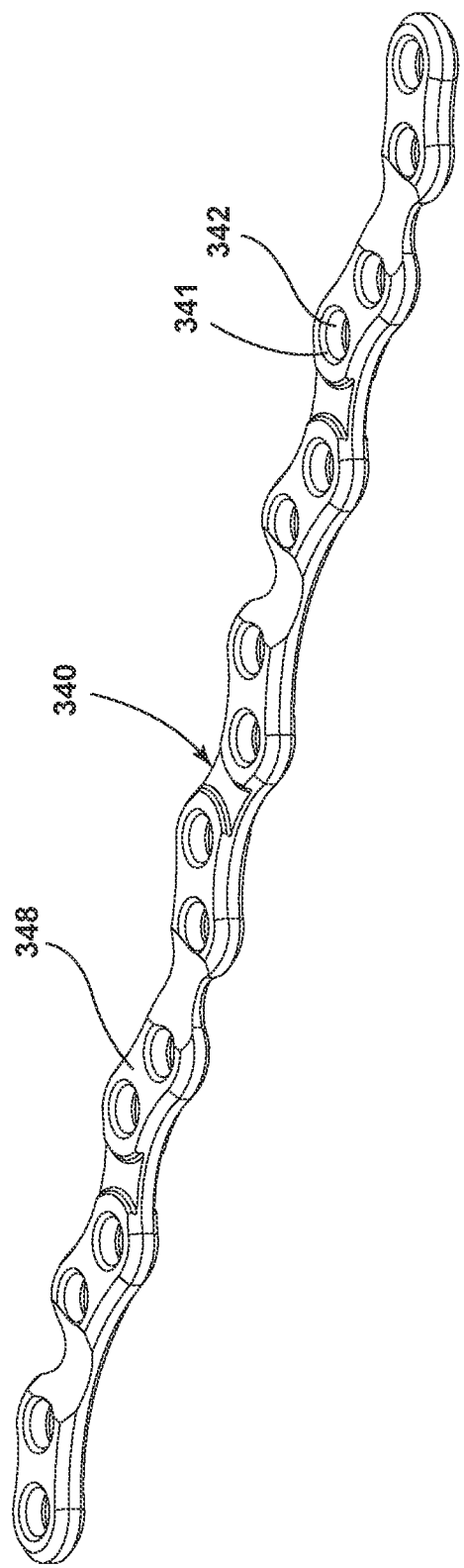
FIG. 22 is a front perspective view of another embodiment of a bone plate.
Figure 23:
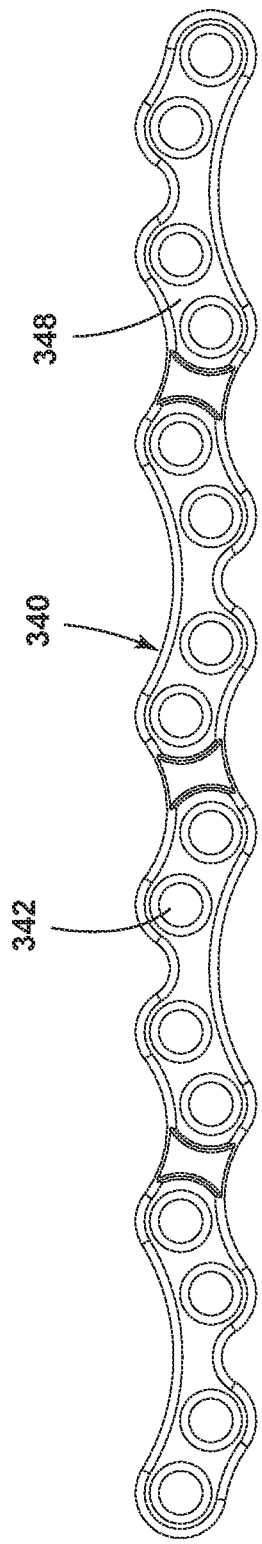
FIG. 23 is a top view of the bone plate shown in FIG. 22.
Figure 24:
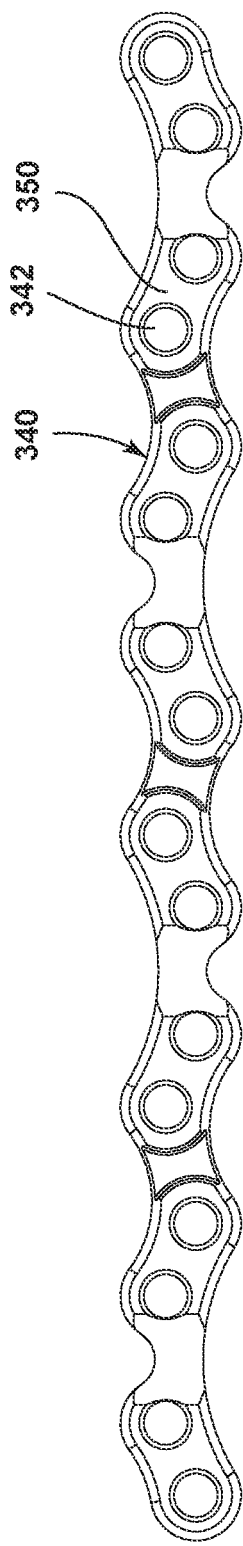
FIG. 24 is a bottom view of the bone plate shown in FIG. 22.
Figure 31:
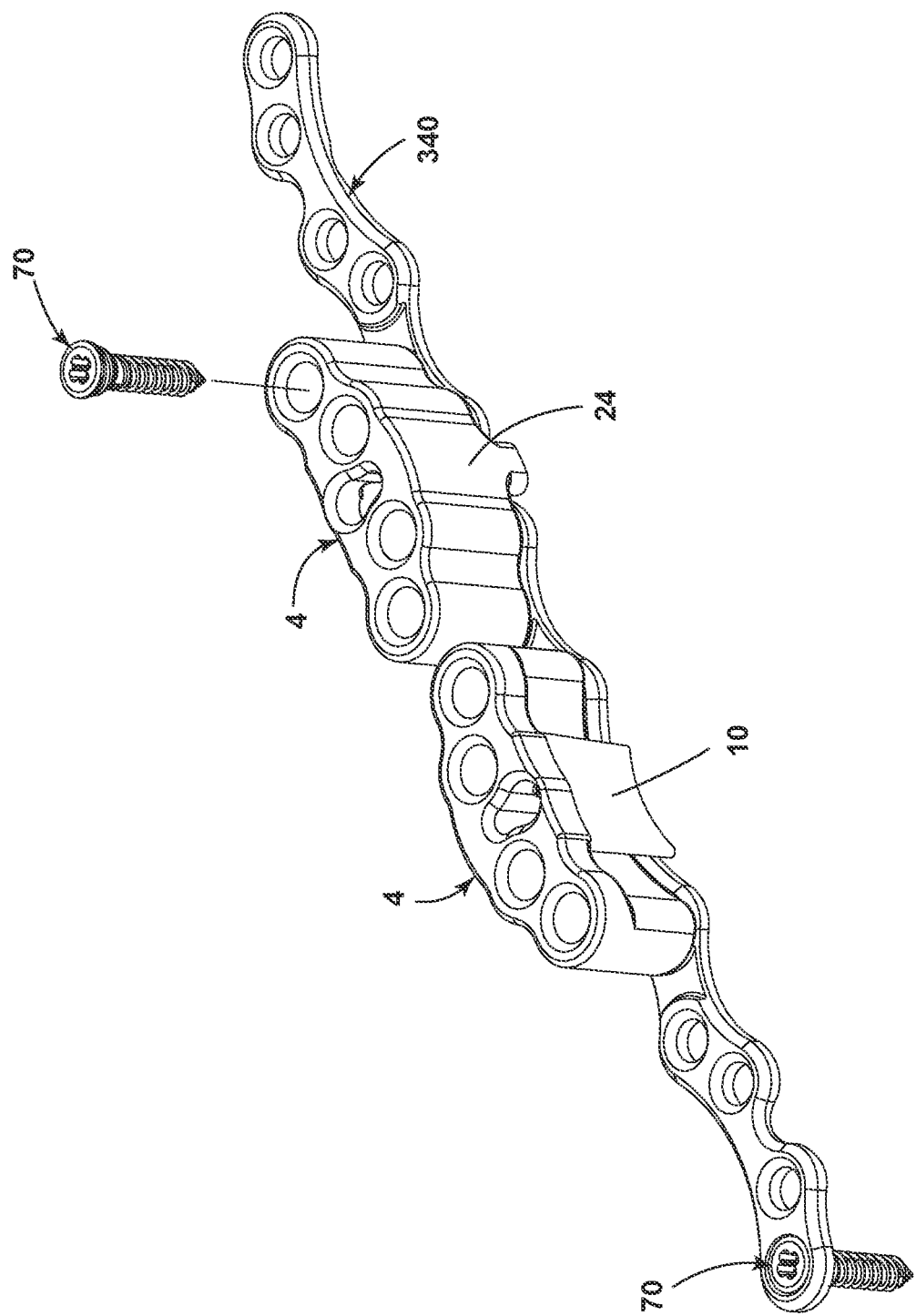
FIG. 31 is a perspective view of the bone plate shown in FIG. 22 utilizing the fastener caddies shown in FIG. 25.
Figure 32:
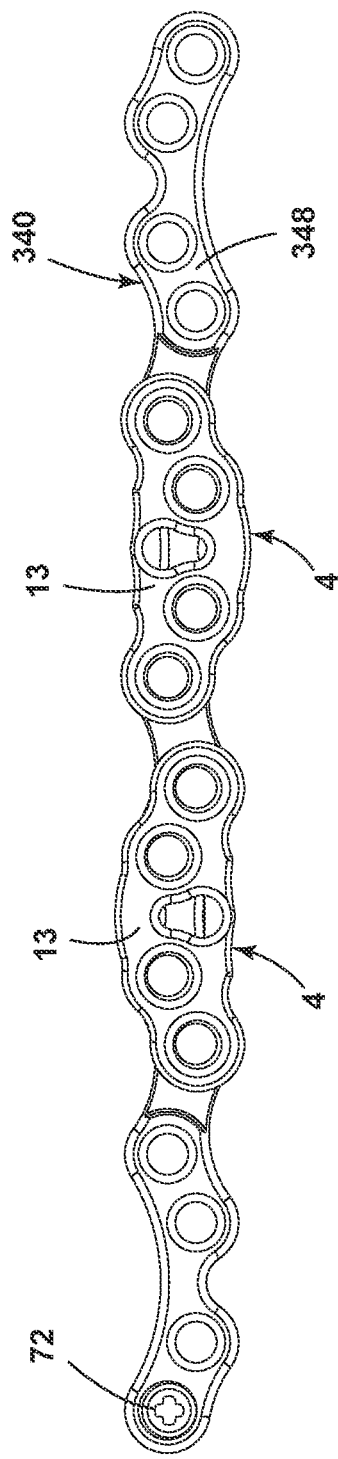
FIG. 32 is a top perspective view of the assembly shown in FIG. 31.
Figure 33:
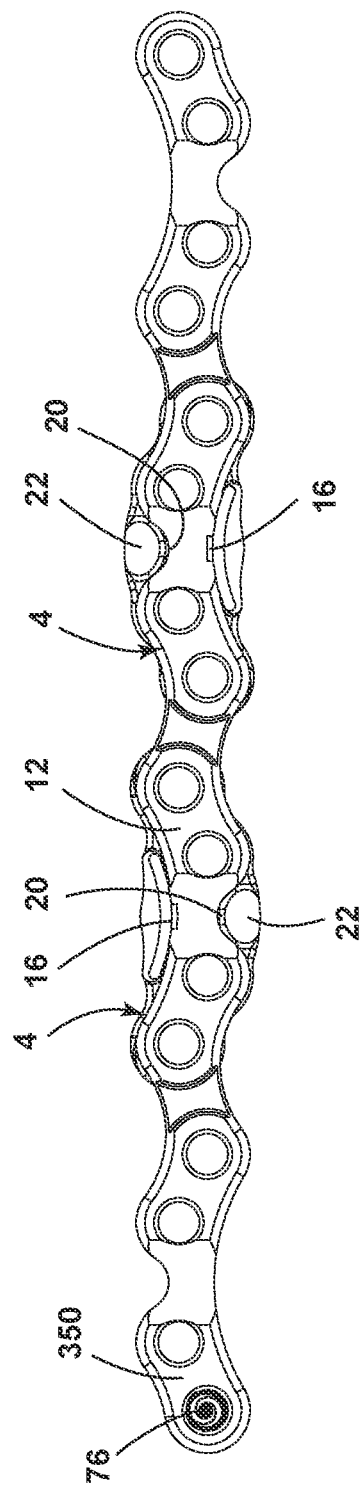
FIG. 33 is a bottom view of the assembly shown in FIG. 31.
Figure 34:
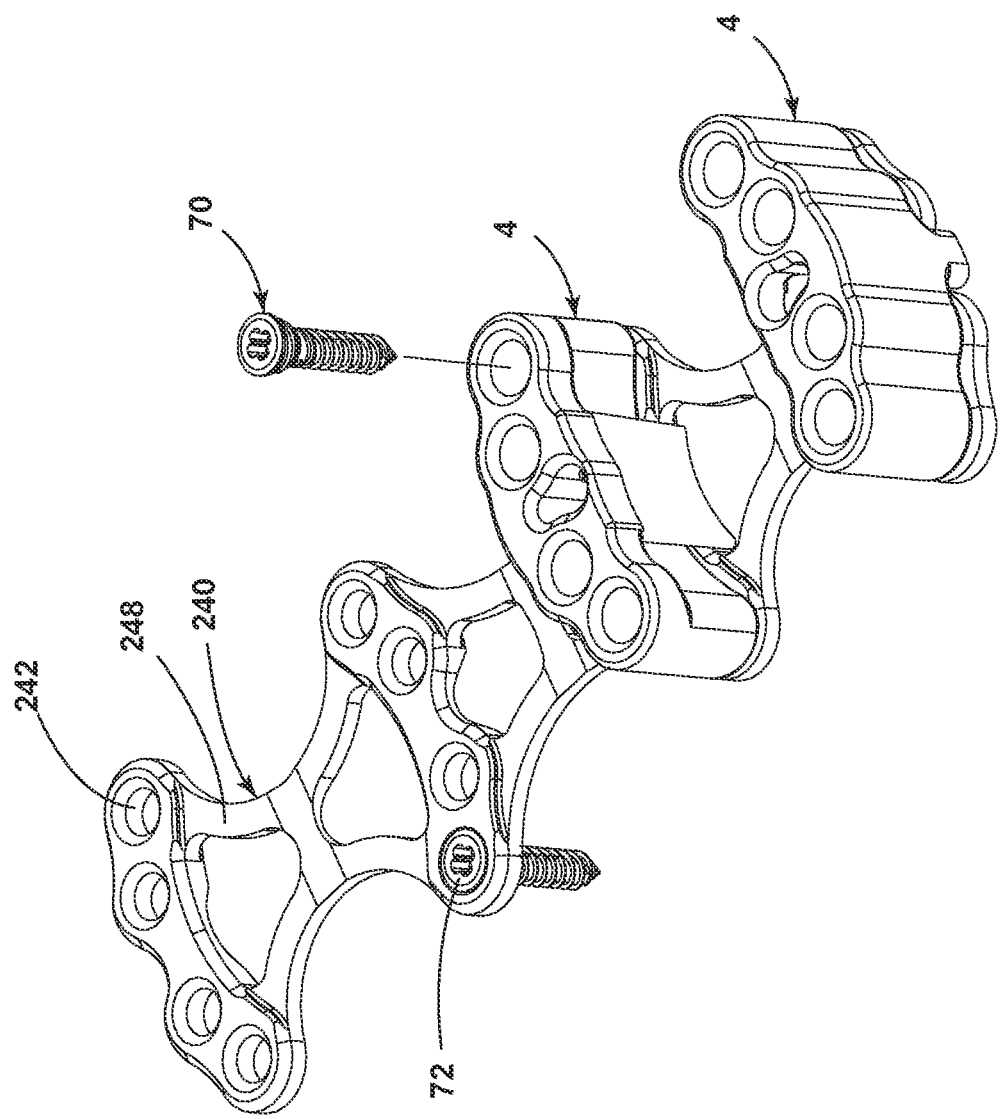
FIG. 34 is a front perspective view of the bone plate shown in FIG. 19 with the fastener caddy shown in FIG. 25.
Figure 36:
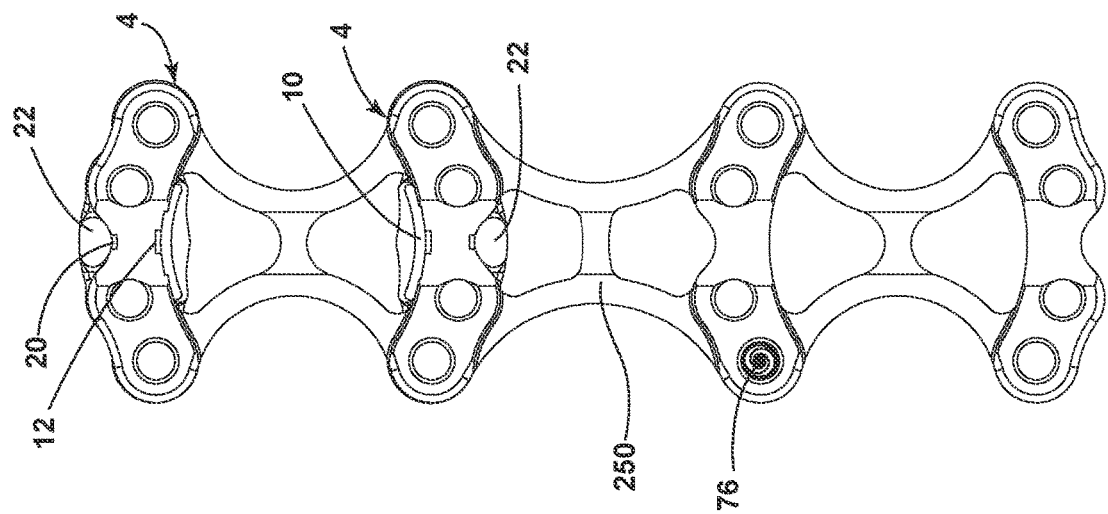
FIG. 36 is a bottom view of the bone plate and fastener caddy assembly shown in FIG. 34.
Figure 35:
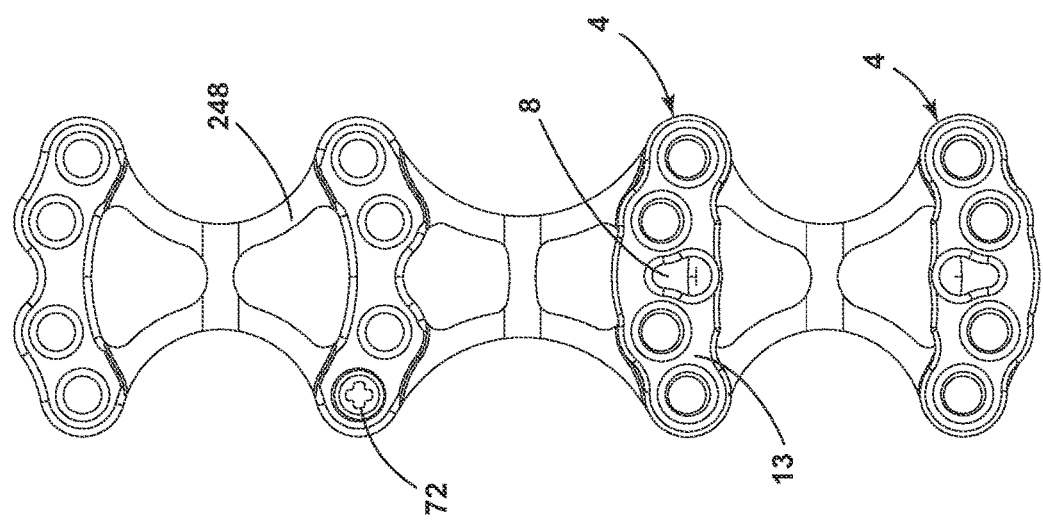
FIG. 35 is a top view of the bone plate and fastener caddy assembly shown in FIG. 34.

FIGS. 16-18 illustrate another embodiment of a bone plate 140. That bone plate 140 has a plurality of fasteners apertures 142 with a rim 141 that will engage a portion of the head 72 of fastener 70 when the fastener 70 is fully installed into the fastener aperture 142. The bone plate 140 has a top surface 148 and a bottom surface 150. FIGS. 19-21 illustrate another embodiment of a bone plate 240. This embodiment also includes a plurality of fastener openings 242 with a rim 241. The bone plate 240 has a top surface 248 and a bottom surface 250. FIGS. 22-24 illustrate another embodiment of a bone plate 340. That bone plate 340 includes a top surface 348, a bottom surface 350, and a number of fastener apertures 342 having a rim 341. FIGS. 31-33 illustrate the use of two fastener caddies 4 on segments of bone plate 340. Similarly, FIGS. 34-36 illustrate the use of multiple fastener caddies 4 on segments of bone plate 240. As can be seen from these embodiments, multiple fastener caddies 4 can be used with a given bone plate, and the fastener caddies 4 can be placed along the length, width, or other positions on the bone plate.

Figure 26:
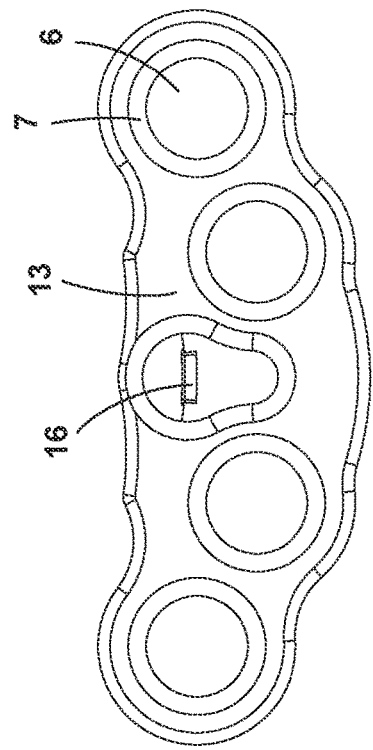
FIG. 26 is a top view of the fastener caddy shown in FIG. 25.
Figure 27:
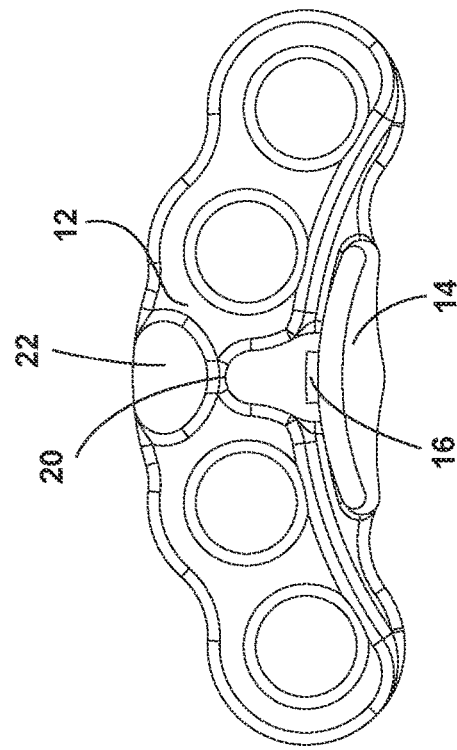
FIG. 27 is a bottom view of the fastener caddy shown in FIG. 25.
Figure 25:
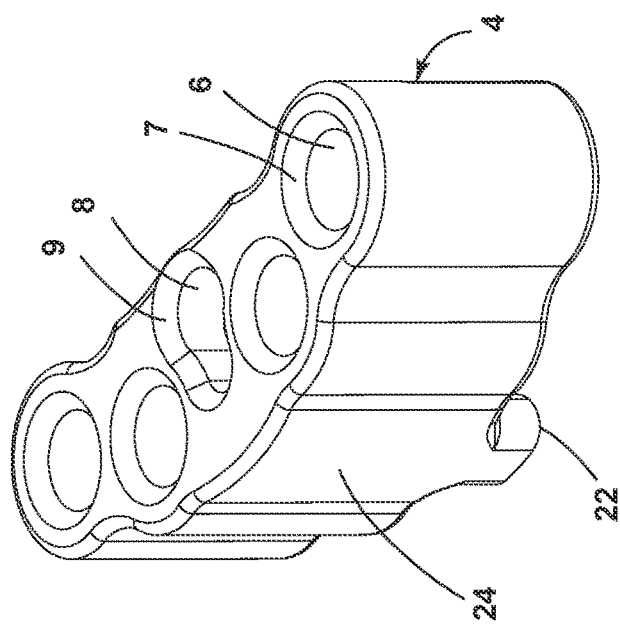
FIG. 25 is a side perspective view of one embodiment of a fastener caddy.
Figure 29:
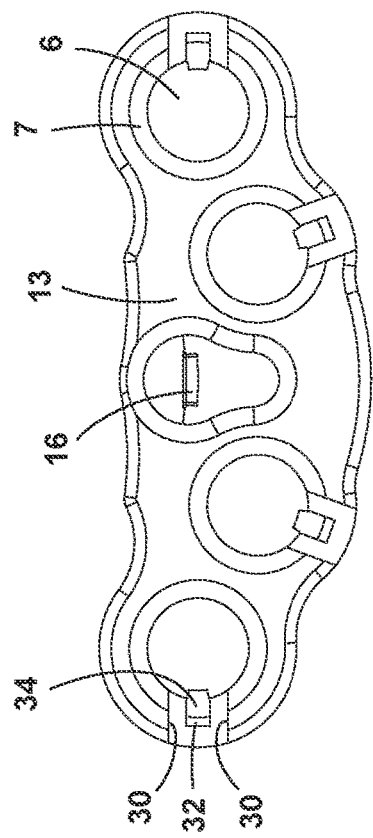
FIG. 29 is a top view of the fastener caddy shown in FIG. 28.
Figure 30:
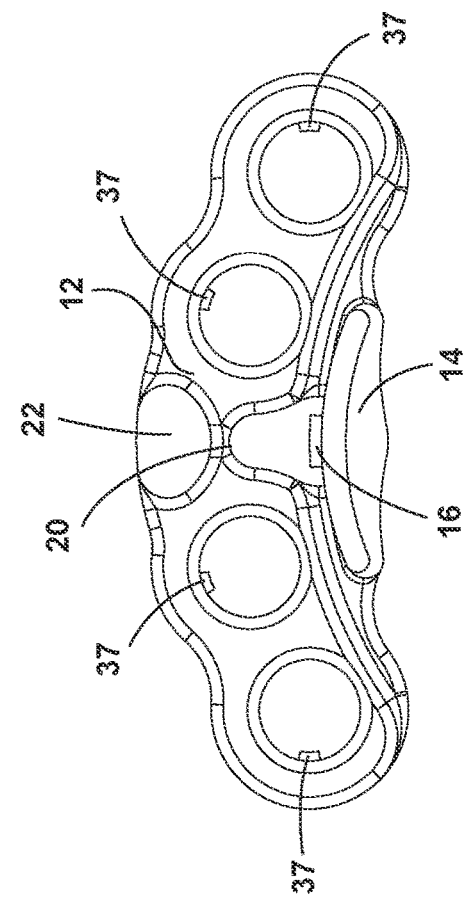
FIG. 30 is a bottom view of the fastener caddy shown in FIG. 28.
Figure 28:
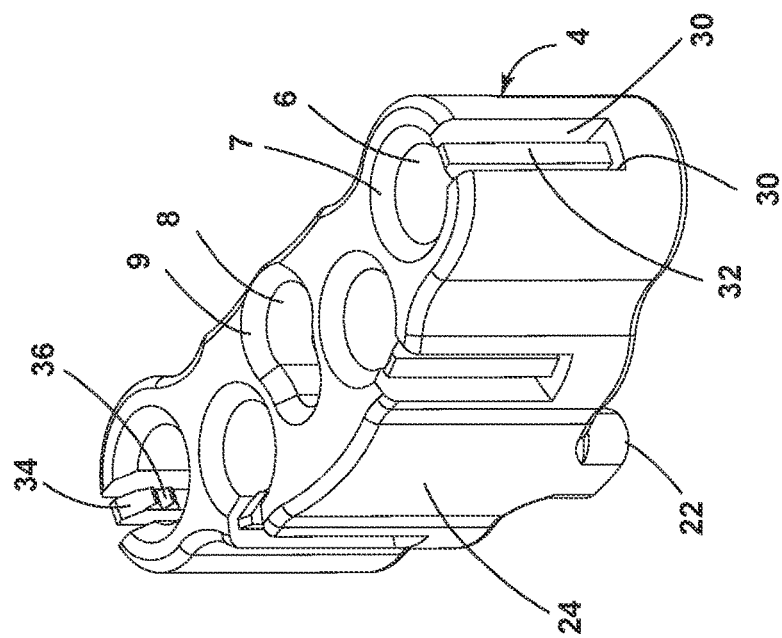
FIG. 28 is a side perspective view of another embodiment of a fastener caddy.

FIGS. 25-27 illustrate an alternative embodiment of the fastener caddy 4. The fastener caddy 4 in that embodiment does not utilize fingers 32.

Figure 37:
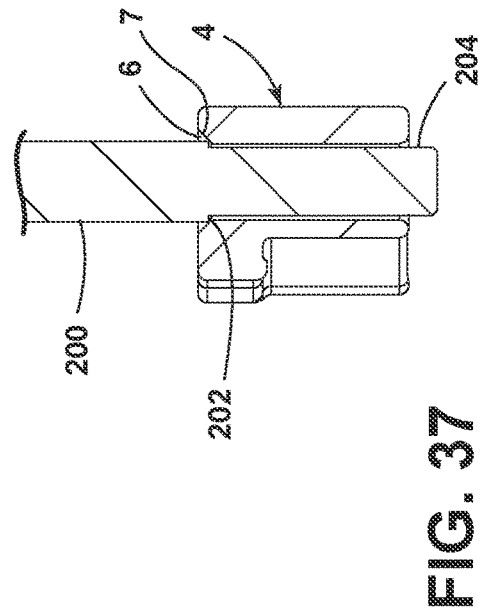
FIG. 37 is a partial cross-sectional view of an insertion tool within a fastener aperture of the fastener caddy.
Figure 40:
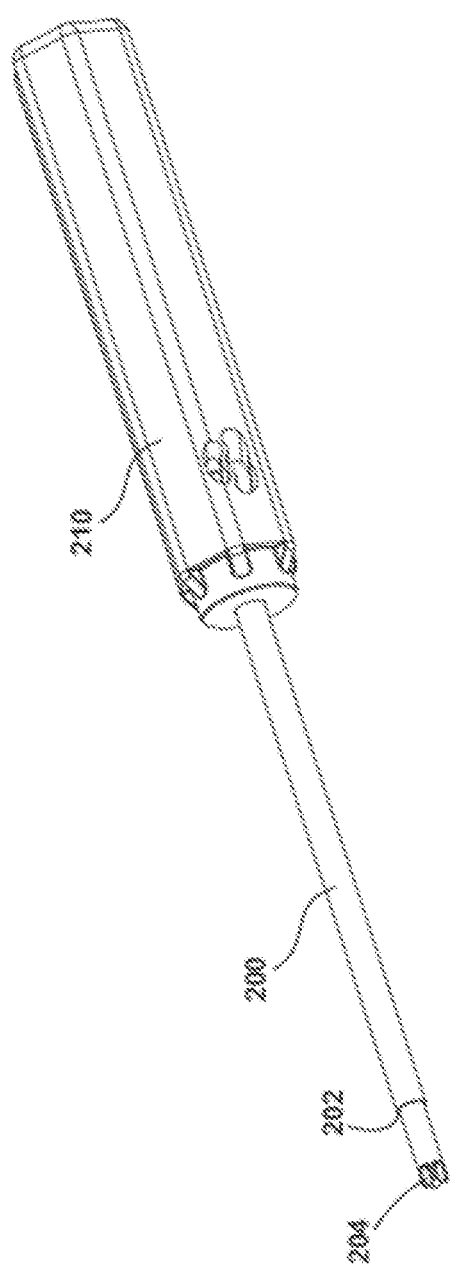
FIG. 40 is a side perspective view of the insertion tool with a handle.
Figure 41:
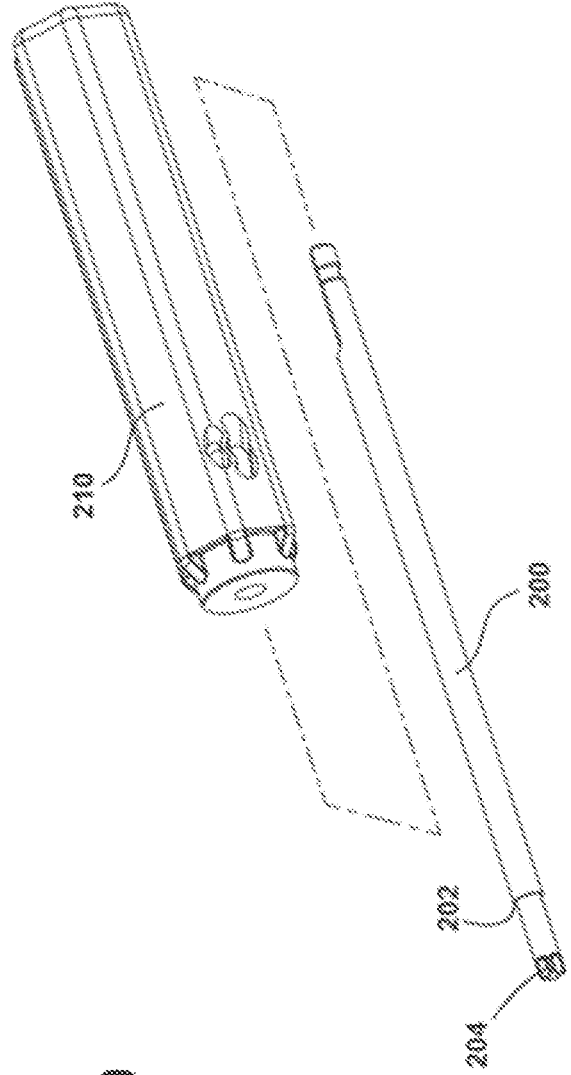
FIG. 41 is a side perspective view of the insertion tool with the handle removed.

The insertion tool 200 is illustrated in FIGS. 40 and 41. The insertion tool 200 can be attached to a handle 210 for manual operation or to a powered device, such as a drill or driver. The insertion tool 200 has a head 204 and a shoulder 202. The head 204 can be shaped so that the insertion tool 200 can drive the fasteners 70 in fastener aperture 6, as illustrated in FIG. 37. Thus, in the illustrated embodiment, the head 204 of the insertion tool 200 has a Phillips head that drives head 72 of fastener 70. The shoulder 202 on insertion tool 200 is spaced to be at a height necessary to fully driver fastener 70 into fastener aperture 42 in bone plate 40. The shoulder 202 will engage tapered surface 7 of fastener aperture 6 when fully inserted into fastener aperture 6, i.e., after the fastener 70 has been fully driven. The shoulder 202 therefore prevents overtightening of the fastener 70 to bone plate 40 and also is of sufficient length to fully drive the fastener 70 into the fastener opening 42.

Figure 38:
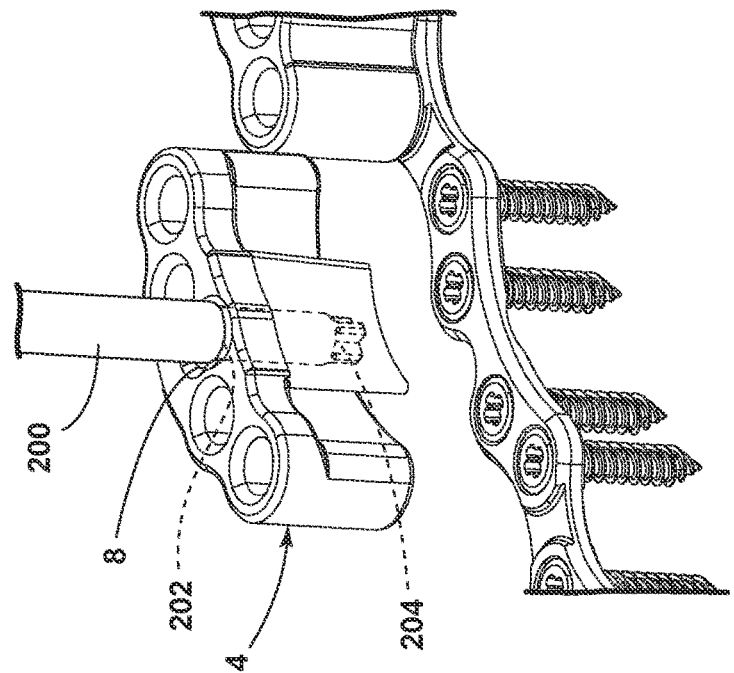
FIG. 38 is a partial front perspective view of an insertion tool being used to remove a fastener caddy from a bone plate.
Figure 39:
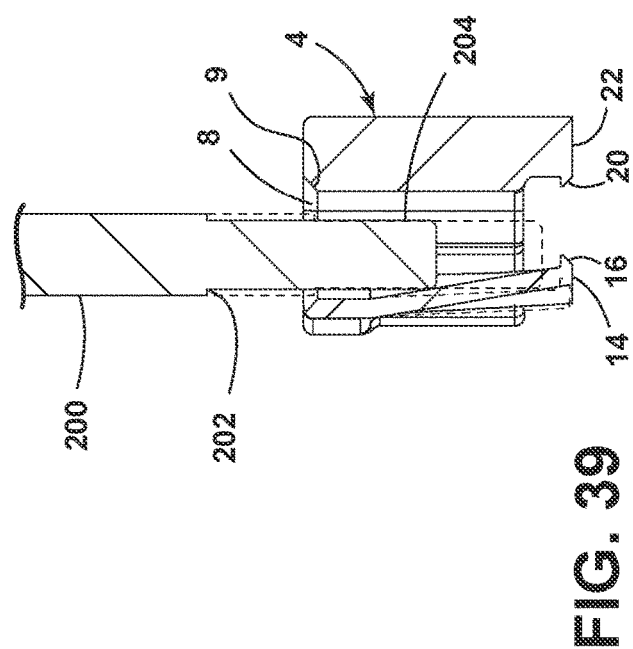
FIG. 39 is a partial cross-sectional view of an insertion tool before it is inserted into the insertion tool aperture in a fastener caddy.

The insertion tool 200 is also used to remove the fastener caddy 4 from the bone plate 40, as illustrated in FIGS. 38-39. The insertion tool 200 will force at least one of the tabs 16, 20 to disengage from the bone plate 40. In the illustrated embodiment of FIG. 39, tab 16 on clip 10 is removed by the advancement of insertion tool 200 into insertion tool aperture 8. The shoulder 202 on insertion tool 200 will be stopped by tapered surface 9 of the insertion tool aperture 8 in the fastener caddy 4.

In use, the fastener caddy 4 has preloaded fasteners 70 in the fastener apertures 6 of the fastener caddy 4. The fastener caddy 4 is coupled to the bone plate 40 by the use of the tabs 16, 20 that engage the lower surface 50 of the bone plate 40. When the fastener caddy 4 is coupled to the bone plate 40, the fastener apertures 6 in the fastener caddy 4 are aligned with the fastener apertures 42 of the bone plate 40. The contours of the sides 3, 5 of the fastener caddy 4 match the contours of the sides 44, 46 of the segment of the bone plate 40 to permit the alignment of the fastener apertures 6, 42. Once the bone plate 40 is aligned on the segment of bone during surgery, the surgeon advances the fasteners 70 through the fastener apertures 6 in fastener caddy 4 until the fasteners 70 are fully installed in the fastener apertures 42 of the bone plate 40. Once the preloaded fasteners 70 in the fastener caddy 4 are advanced into the bone plate 40, the fastener caddy 4 is removed by use of an insertion tool 200 that is inserted into the insertion tool aperture 8. The insertion tool 200 presses against one or both of the clips 10, 24 of the fastener caddy 4 to disengage one or both of tabs 16, 20 from the bottom surface 50 of the bone plate 40 permitting the fastener caddy 4 to be removed laterally and/or upwards.

In the illustrated examples, the lower surface 14 of clip 10 and the bottom surface 22 of clip 24 do not extend beyond the bottom surface 50 of bone plate 40. That is because bone plate 40 has an indented surface 53 in the area of tabs 16, 20. This permits the portions of the bone plate 40 to rest directly against the bone and to permit removal of the fastener caddy 4 from bone plate 40 once all fasteners 70 have been installed.

The fastener caddy 4 can be made of any suitable material that permits one or more of the clips 10, 24 to be deflected by the insertion tool. The fastener caddy 4 can be made from a polymeric material, metal, or a combination thereof. For example, the fastener caddy 4 can be made by injection molding a polymeric material, such as plastic and/or resin. The fastener caddy 4 can also be machined or stamped from a polymeric or metal material. The fastener caddy 4 can also be made from additive manufacturing or 3D printing. The flexibility of the material used in the fastener caddy 4 permits the installation of the fasteners 70 into the bone plate 40 by permitting the tapered portion of the head 72 to deflect the sides of the fastener opening 6 as the fastener 70 is advanced toward the bone plate 40.

Figure 45:
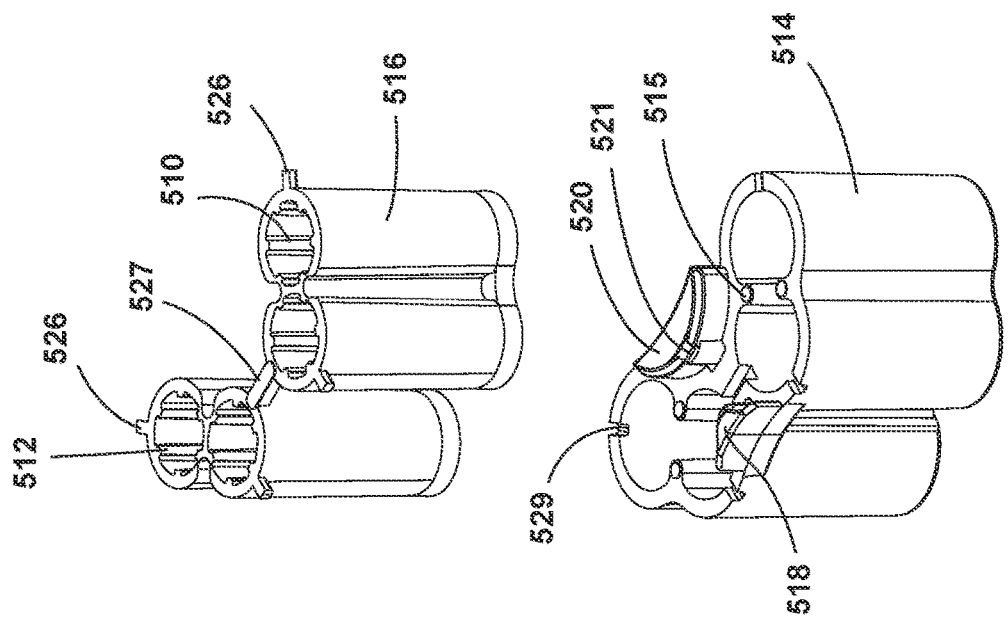
FIG. 45 is a top perspective view of the components of the fastener caddy shown in FIG. 42.
Figure 44:
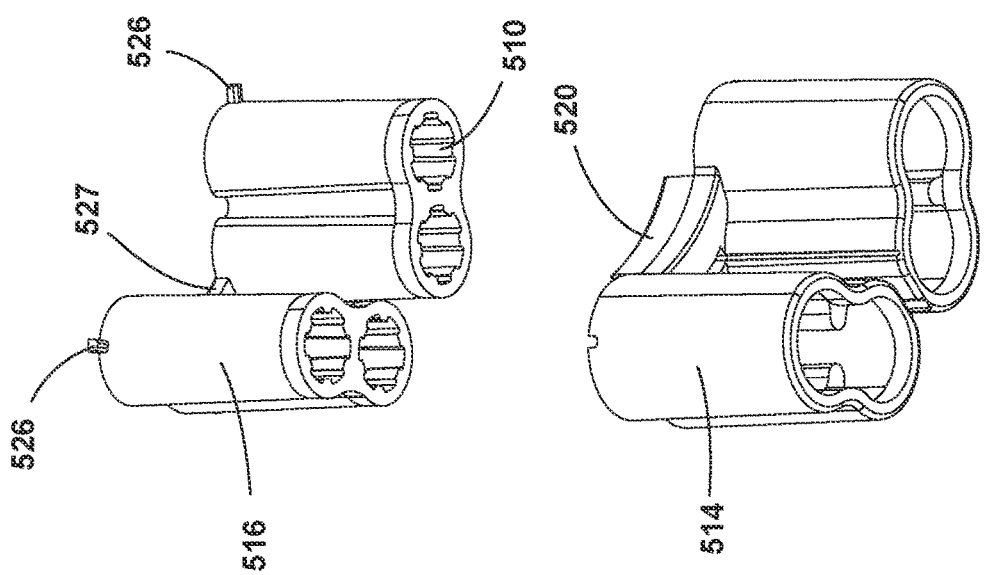
FIG. 44. is a bottom perspective view of the components of the fastener caddy shown in FIG. 42.
Figure 47:
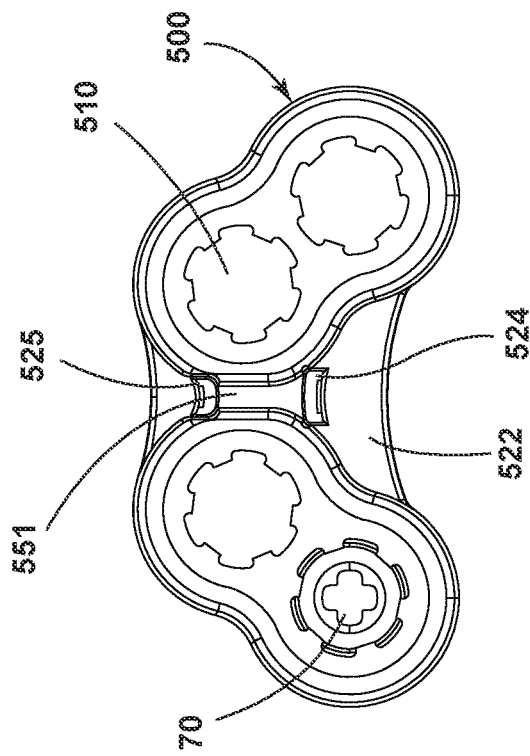
FIG. 47 is a top view of the fastener caddy shown in FIG. 42 with a fastener inserted.
Figure 46:
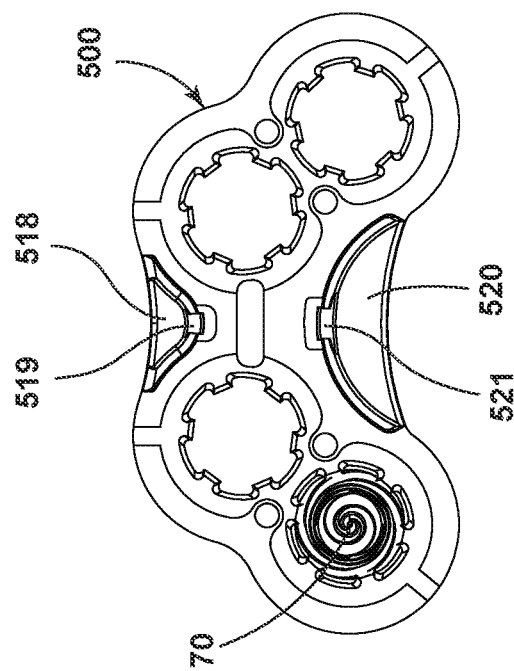
FIG. 46 is a bottom view of the fastener caddy shown in FIG. 42 with a fastener inserted.
Figure 49:
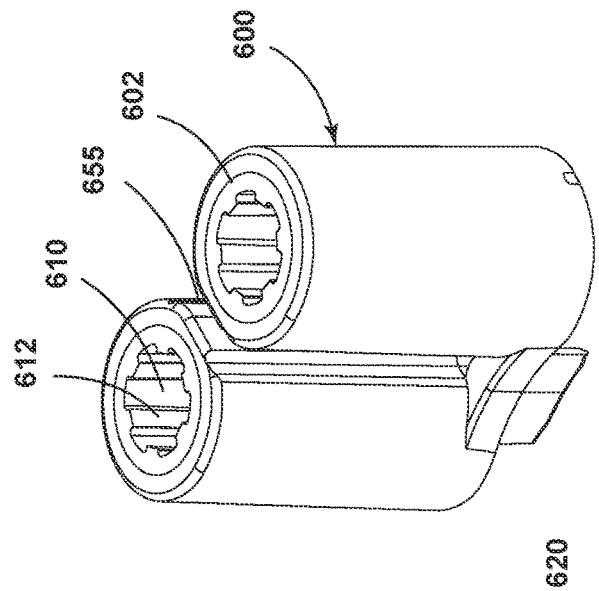
FIG. 49 is a top view of the fastener caddy shown in FIG. 48.
Figure 48:
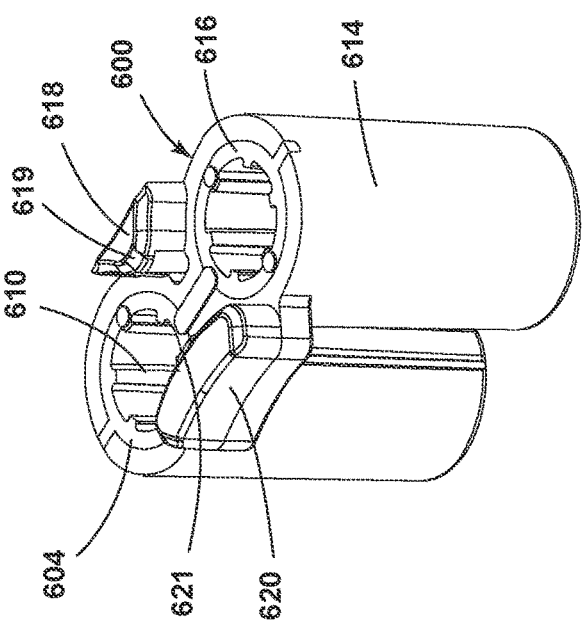
FIG. 48 is a bottom perspective view of another embodiment of a fastener caddy.
Figure 51:
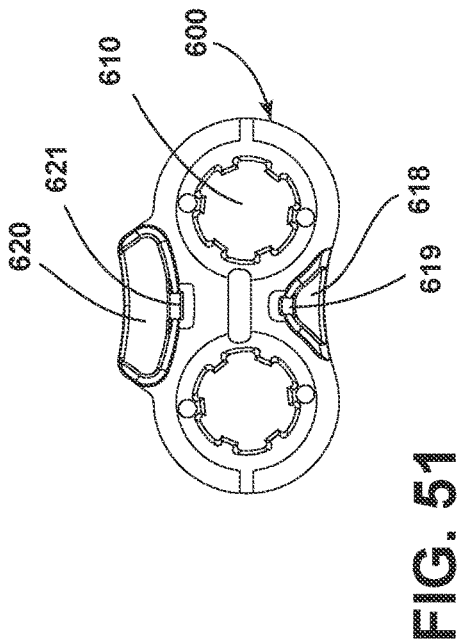
FIG. 51 is a bottom view of the fastener caddy shown in FIG. 48.
Figure 50:
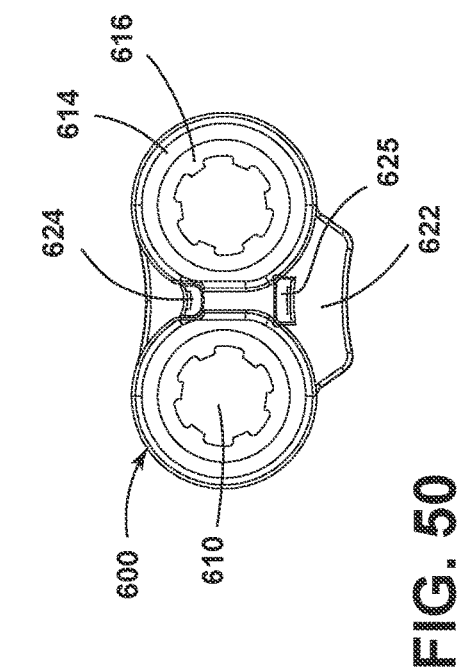
FIG. 50 is a top perspective view of the fastener caddy shown in FIG. 48.
Figure 53:
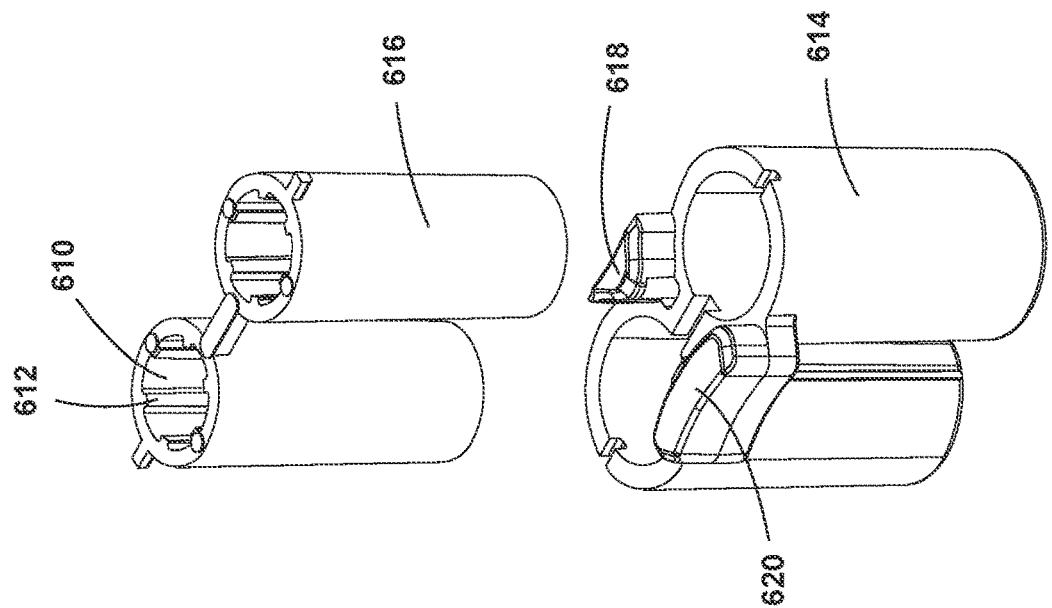
FIG. 53 is a bottom perspective view of the components of the fastener caddy shown in FIG. 48.
Figure 52:
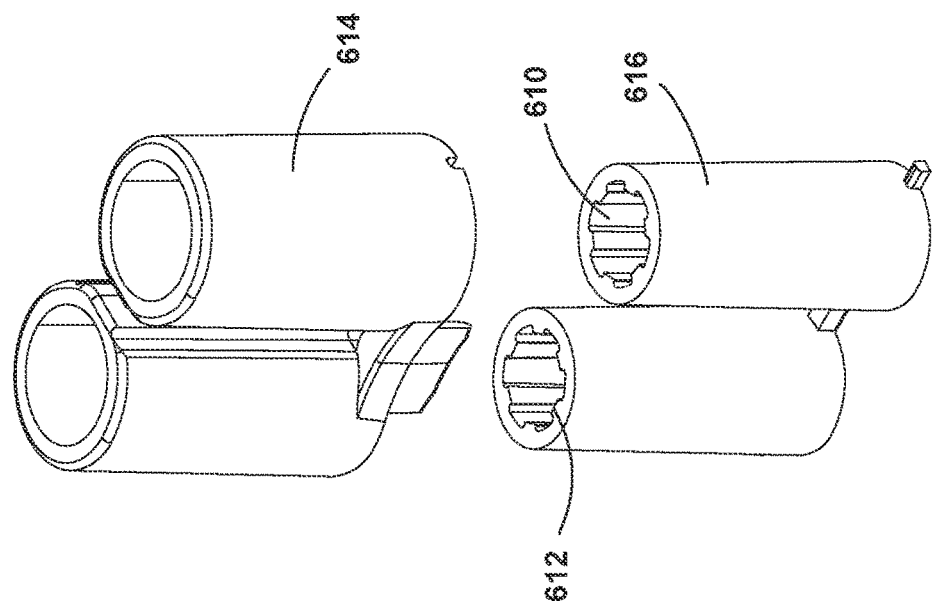
FIG. 52 is a top perspective view of the components of the fastener caddy shown in FIG. 48.

Another embodiment of a fastener caddy 500 is illustrated in FIGS. 42-47. The fastener caddy 500 has a top surface 502 and a bottom surface 504. The fastener caddy 500 includes a number of fastener apertures 510 extending between the top surface 502 and bottom surface 504, with ribs 512 on the interior surface of the fastener apertures 510. The ribs 512 help hold the fastener 70 in place and can deflect as the fastener 70 is advanced into the bone plate 700. Fastener caddy 500 includes a shell 514 which can be made of a harder material, such as acrylonitrile butadiene styrene (ABS) or other hard polymeric material, and an elastomeric portion 516 that can be made of a more flexible material, such as a thermoplastic elastomer. The shell 514 and the elastomeric portion 516 can be made from a multi-step molding process. For example, the shell 514 can be molded first, with the elastomeric portion 516 being molded thereafter. The elastomeric portion 516 is shown as having a connection 527 to permit the elastomeric material to travel between separate fastener apertures 510 during the molding process. In addition, the elastomeric portion 516 can include sections 526 which help secure the elastomeric portion 516 to the shell 514 to prevent or limit the rotation of the elastomeric portion 516 within the shell 514. In addition, the shell 514 can include raised portions 515, to help strengthen the area between adjoining fastener apertures 510. Alternatively, the shell 514 and the elastomeric portion 516 can be formed as separate pieces, and then coupled together by insertion of the elastomeric portion 516 into the shell 514 such that the sections 526 of elastomeric portion 516 fit into grooves 529 on shell 514, as shown in FIGS. 44 and 45.

The fastener caddy 500 includes a first clip 520 with a tab 521 on one side of the fastener caddy 500 and a second clip 518 with a tab 519 on the other side of the fastener caddy 500. As illustrated in FIGS. 74 and 75, the first clip 520 with tab 21 and the second clip 518 with tab 519 can couple to the bone plate 700 in a similar manner as the fastener caddy 4 couples to the bone plate 40. The fastener caddy 500 includes central portion 522 located between each pair of fastener apertures 510. The central portion 522 can include a gap 551 between the two pairs of fastener apertures 510. The central portion 522 can also include openings 524, 525. The gap 551 and the openings 524, 525 can help facilitate the removal of the fastener caddy 500 from the bone plate 700 once the fasteners 70 have been installed into the bone plate 700 and underlying bone. In the illustrated embodiments of FIGS. 42-47, no insertion tool is necessary to remove the fastener caddy 500 from the bone plate 700. Rather, once the fasteners 70 are advanced into the bone plate 700 and bone, the fastener caddy 500 can be pulled, rocked, and/or twisted off given the flexibility of the fastener caddy 500. The flexibility is due to the materials used in the fastener caddy 500, the gap 551, and the openings 524, 525 in the central portion 522 of fastener caddy 500.

Another embodiment of the fastener caddy 600 is illustrated in FIGS. 48-53. This embodiment is similar to the fastener caddy 500, with the exception that there is a single fastener aperture 610 on each side of the fastener caddy 600. The fastener caddy 600 includes a top surface 602 and a bottom surface 604. The fastener apertures 610 extends from the top surface 602 to the bottom surface 604 and has internal ribs 612. The central portion 622 of fastener caddy 600 includes openings 624, 625 and a gap 655 in between the two fastener apertures 610. Fastener caddy 600 also has a first clip 620 with a tab 621 and a second clip 618 with a tab 619 to help facilitate the coupling of the fastener caddy 600 to the bone plate 700. The fastener caddy 600 can include a shell 614 and an elastomeric portion 616 that are coupled together either as separate shots within a molding process or the coupling of separate pieces together, as described above in the context of fastener caddy 500. The fastener caddy 600 can be de-coupled from a bone plate by being pulled, rocked, and/or twisted.

Figure 54:
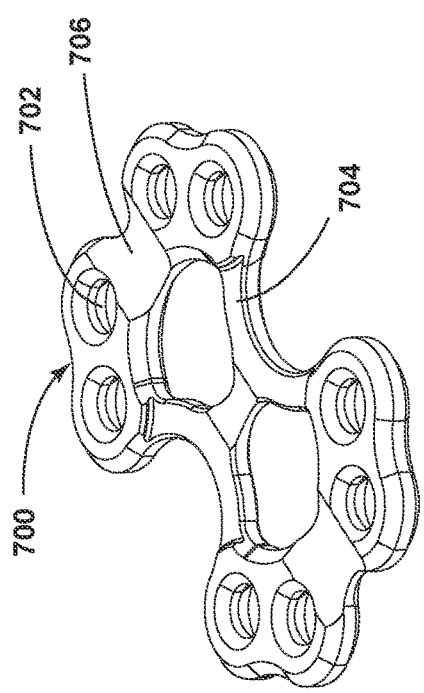
FIG. 54 is a front perspective view of another embodiment of a bone plate.
Figure 56:
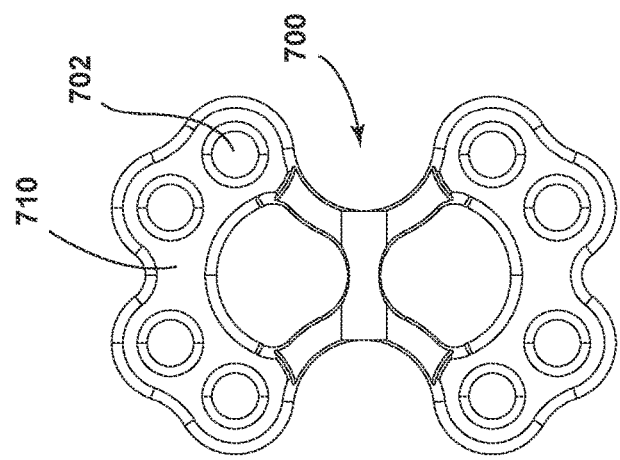
FIG. 56 is a top view of the bone plate shown in FIG. 54.
Figure 55:
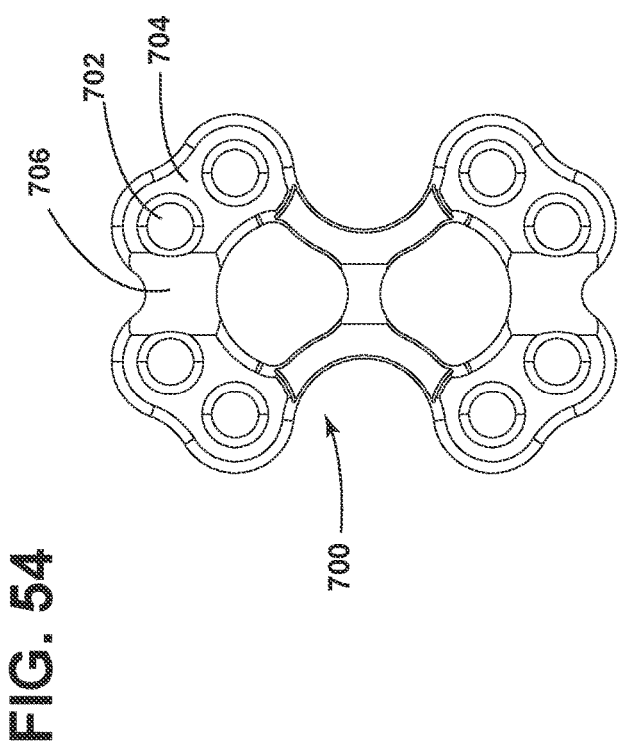
FIG. 55 is a bottom view of the bone plate shown in FIG. 54.

Another embodiment of a bone plate 700 is shown in FIGS. 54-56. This bone plate 700 includes fastener apertures 702 in between a top surface 710 and a bottom surface 704. The bone plate 700 includes indented sections 706 on the bottom surface 704 which can receive portions of the first clip 520 and tab 521 and second clip 518 and tab 519 of fastener caddy 500 such that the bottom surface first clip 520 and second clip 518 do not protrude beyond the bottom surface 704 of bone plate 700. Thus, when in use, when the fastener caddy 500 is coupled to bone plate 700, the bone plate 700 can rest directly against the bone. The indented sections 706 also assisting in the separation of the fastener caddy 500 from the bone plate 700. Fastener caddy 600 will be similarly coupled to the ends of bone plate 700, although that may result in only four fasteners 70 being installed in the bone plate 700 if fastener caddy 600 is utilized.

Figure 57:
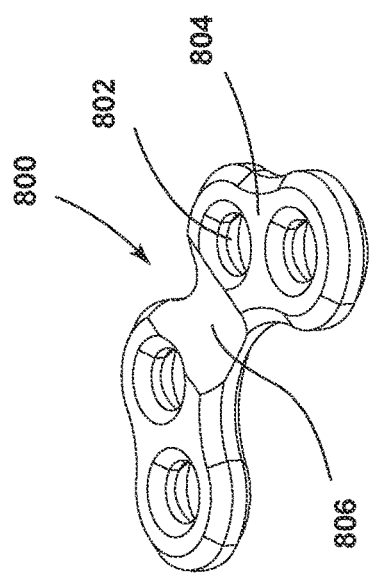
FIG. 57 is a front perspective view of another embodiment of a bone plate.
Figure 59:
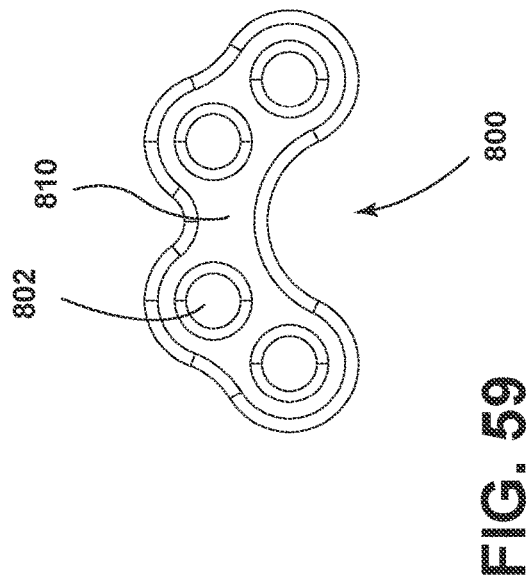
FIG. 59 is a top view of the bone plate shown in FIG. 57.
Figure 58:
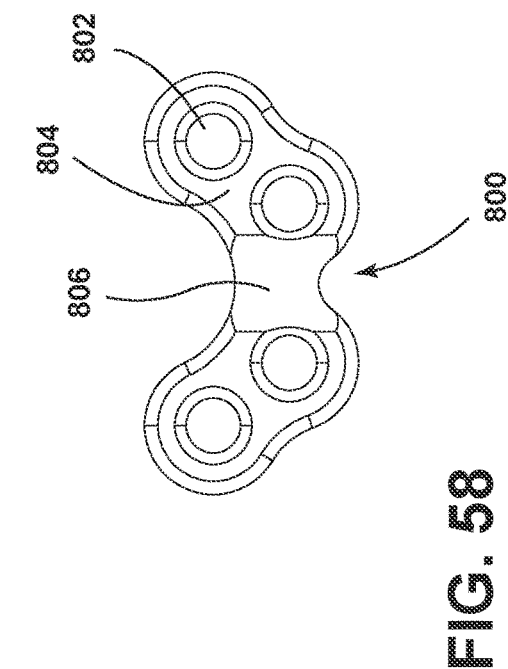
FIG. 58 is a bottom view of the bone plate shown in FIG. 57.

Another bone plate 800 is illustrated in FIGS. 57-59 which can, again, be utilized with any of the aforementioned described fastener caddies 4, 500, or 600. Bone plate 800 includes fastener apertures 802 that extend between the top surface 810 and the bottom surface 804. The bottom surface 804 includes indented sections 806 which assist in the coupling of the fastener caddies 4, 500, 600 to the bone plate 800 and in the removal of the fastener caddies 4, 500, 600 from bone plate 800.

Figure 60:
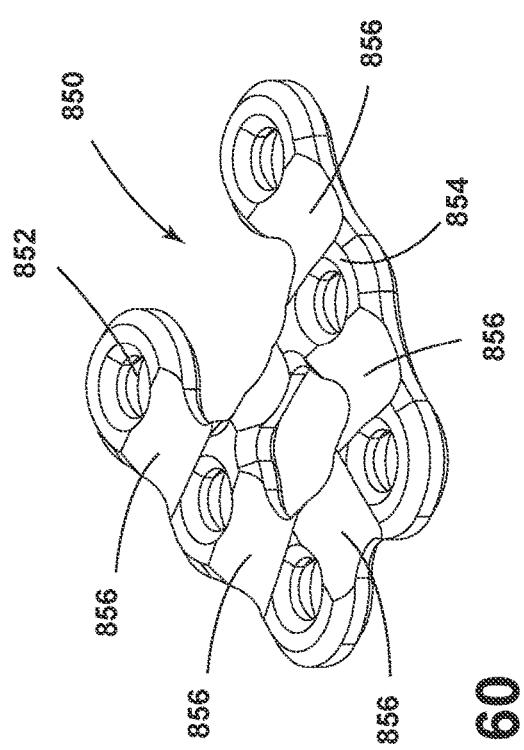
FIG. 60 is a front perspective view of another embodiment of a bone plate.
Figure 62:
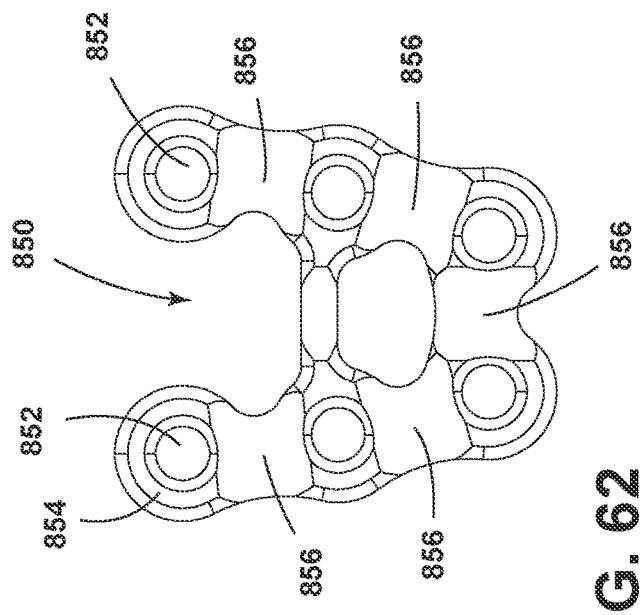
FIG. 62 is a bottom view of the bone plate shown in FIG. 60.
Figure 61:
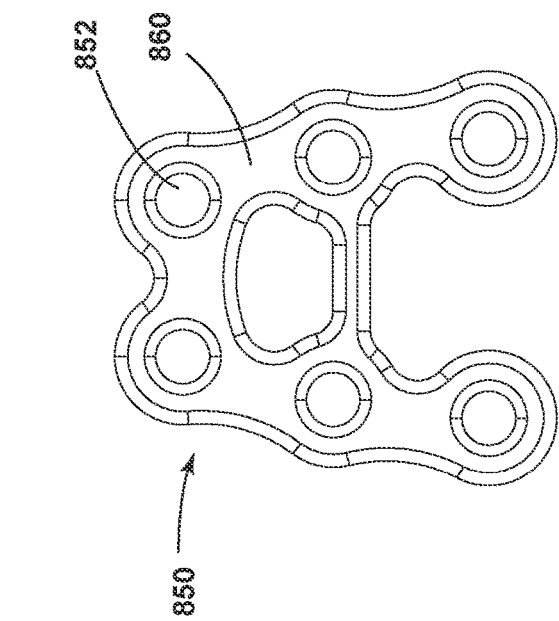
FIG. 61 is a top view of the bone plate shown in FIG. 60.

Another embodiment of a bone plate 850 is illustrated in FIGS. 60-62. The bone plate 850 includes fastener apertures 852 which extend from top surface 860 to bottom surface 854. The bottom surface 854 includes indented sections 856 which assist in the coupling of the fastener caddies 4, 500, 600 to the bone plate 850. Bone plate 850 is particularly adapted for use with fastener caddy 600 as the indented sections 856 are between adjacent fastener openings 852.

Yet another embodiment of a bone plate 900 is illustrated in FIGS. 63-65. Bone plate 900 includes fastener apertures 902 that extend between the top surface 910 and the bottom surface 904. Bone plate 900 similarly has indented sections 906 in between adjacent pairs of fastener apertures 902, and is, thus, more particularly adapted for use with fastener caddies 4 and 500.

Figure 68:
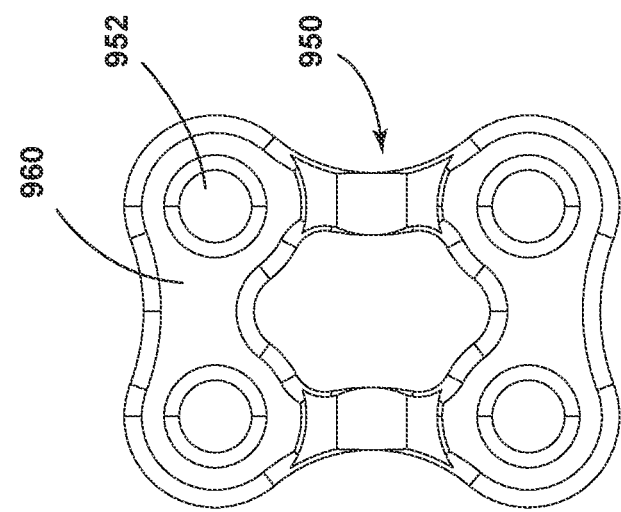
FIG. 68 is a top view of the bone plate shown in FIG. 66.
Figure 66:
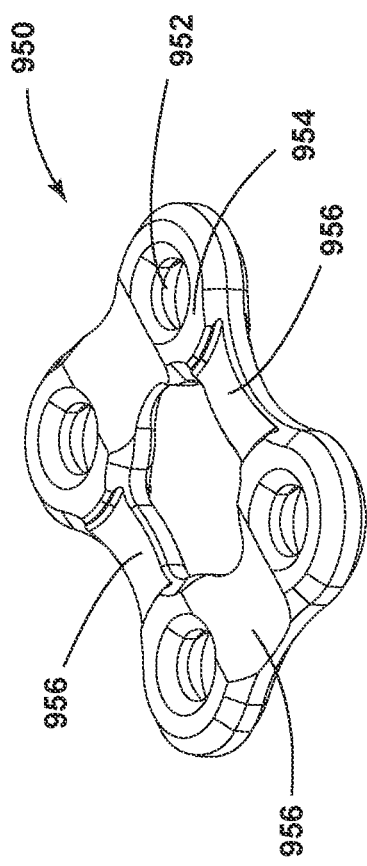
FIG. 66 is a front perspective view of another embodiment of a bone plate.
Figure 67:
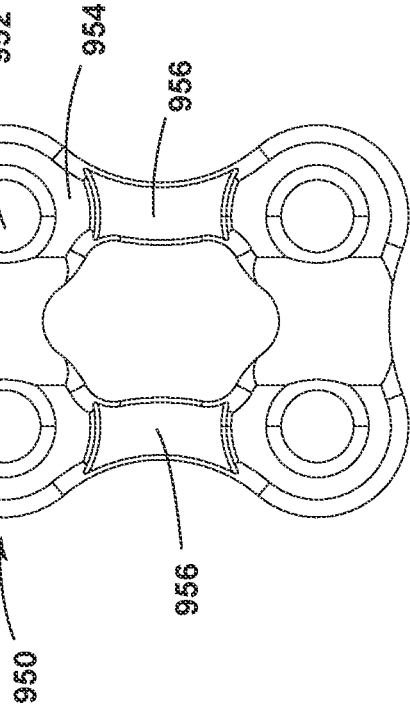
FIG. 67 is a bottom view of the bone plate shown in FIG. 66.

Another embodiment of a bone plate 950 is illustrated in FIGS. 66-68. This bone plate 950 includes fastener apertures 952 between the top surface 960 and bottom surface 954. The bone plate 950 also includes an indented section 956 in between adjacent fastener apertures 510, and is, thus, particularly adapted for use with fastener caddy 600.

Yet another embodiment of a bone plate 970 is illustrated in FIGS. 69-71. Bone plate 970 includes fastener apertures 972 located between the top surface 975 and bottom surface 974. The bone plate 970 includes indented sections 976 on the bottom surface 974 and is particularly adapted for use with fastener caddy 500.

Figure 72:
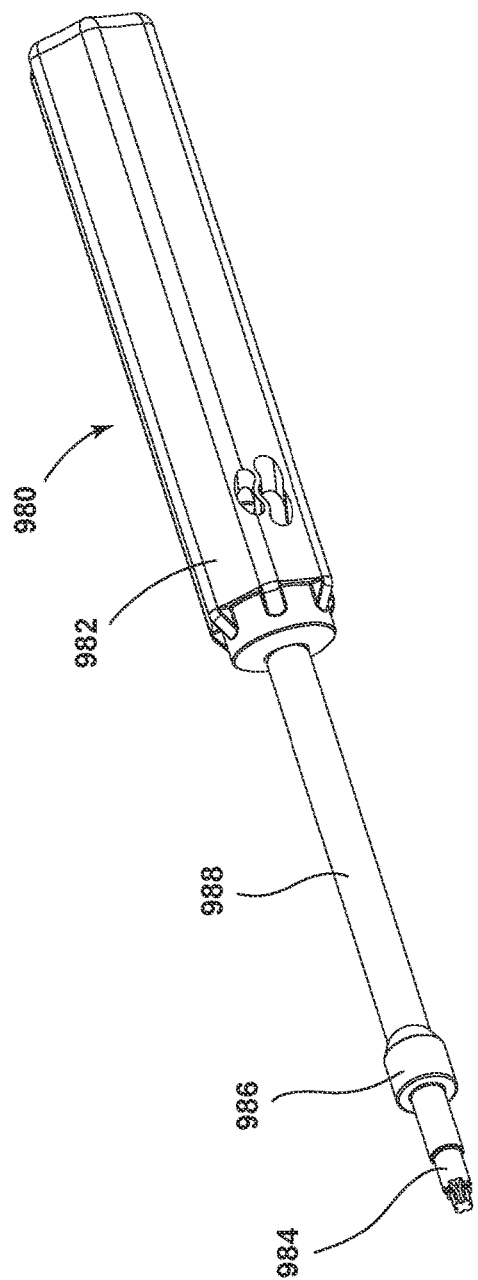
FIG. 72 is a side perspective view of an embodiment of a driver.
Figure 73:
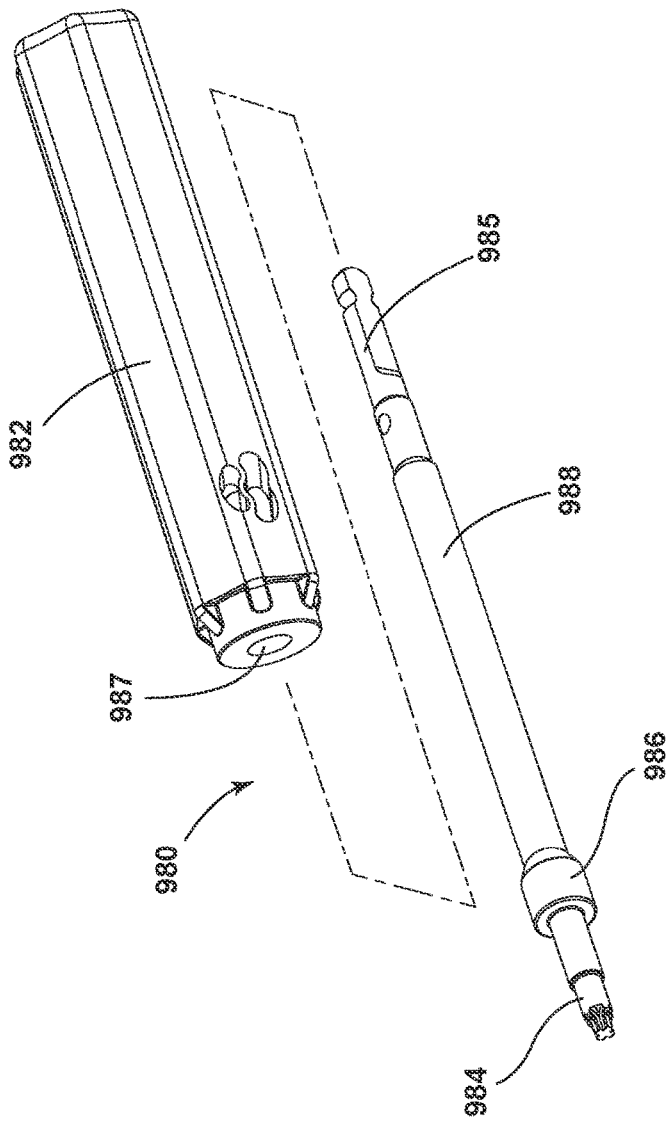
FIG. 73 is a side perspective view of the components of the driver shown in FIG. 72.

Another embodiment of a driving tool is illustrated in FIGS. 72 and 73. As described above, fastener caddies 500, 600 do not require the use of an insertion tool to remove the fastener caddy 500, 600 from the bone plate 700, 800, 850, 900, 950, or 970. Driving tool 980 includes a handle 982 that is coupled to a shaft 988 that has a head 984 that can be used to drive fasteners 70. The shaft 988 includes an expanded section 986 and a coupling 985 that is received within opening 987 of handle 982.

As illustrated in FIGS. 74 and 75, the installation of fastener caddy 500 to bone plate 700 can be done with the fastener 70 preloaded into fastener caddy 500. When fastener caddy 500 is installed on bone plate 700, the first clip 520 and associated tab 521 and the second clip 518 and associated tab 519 contact indented sections 706 on the bottom surface 704 of bone plate 700.

The bone plate 40 can also be made of a biocompatible polymeric and/or metal material that is suitable for installation to the bone. Similarly, the fasteners 70 can also be made of a biocompatible polymeric and/or metal material.

The shape of the fastener caddy 4 can vary depending upon the shape of the bone plate 40. The shape of the fastener caddy 4 will require the alignment of the fastener aperture 6 in the fastener caddy 4 with the fastener aperture 42 in the bone plate 40. The shape of the fastener caddy 4 will also require at least one clip with a tab that can engage a lower surface of the bone plate 40.

While the illustrated embodiments show the fastener caddies 4, 500, 600 being coupled to bone plates 40, 700, etc. by the use of a clipping mechanism, the fastener caddies 4, 500, 600 could be coupled to the bone plates 40, 700, etc. by other mechanisms. For example, the fastener caddies 4, 500, 600 could be coupled to the bone plates 40, 700, etc. by use of one or more removable fasteners, such as screws, adhesive tape, etc. The fastener caddies 4, 500, 600 could also be coupled to the bone plates 40, 700, etc. by use of a releasable liner, such as tape, adhesive, and hook-and-loop fasteners. These securing mechanisms can be used in combination with or instead of the clipping mechanism. Thus, the fastener caddies 4, 500, 600 could be removed from the bone plates 40, 700, etc., by the removal of a removable fastener instead of the flexing of the fastener caddies 4, 500, 600.

The fastener caddy 4, fasteners 70, and bone plate 40 can be packaged together. Thus, a single, sterilized package could contain the fastener caddy 4 coupled to the bone plate 40 with the fasteners 70 already installed in the fastener apertures 6 of the fastener caddy 4. Alternatively, the fastener caddy 4 could be packaged with the fasteners 70 installed or uninstalled. The fastener caddy 4 can be disposable such that once the fasteners 70 are installed into the bone plate 40 and the fastener caddy 4 is decoupled from the bone plate 40, the fastener caddy 4 is disposed. Alternatively, the fastener caddy 4 can be reused if it is sterilized again.

In the foregoing description, it will be readily appreciated by those skilled in the art that modifications may be made to the invention without departing from the concepts disclosed herein. Such modifications are to be considered as included in the following claims, unless these claims by their language expressly state otherwise.

It will be understood by one having ordinary skill in the art that construction of the present disclosure and other components is not limited to any specific material. Other exemplary embodiments of the disclosure disclosed herein may be formed from a wide variety of materials, unless described otherwise herein.

For purposes of this disclosure, the term "coupled" or "operably coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated. In addition, while certain embodiments have shown threaded connections, the threaded connections could include tape or other sealing material in the threaded connection. In addition, the threaded connection could be replaced by other suitable connections or couplings, such as compression couplings or other couplings.

For purposes of this disclosure, the term "connected" or "operably connected" (in all of its forms, connect, connecting, connected, etc.) generally means that one component functions with respect to another component, even if there are other components located between the first and second component, and the term "operable" defines a functional relationship between components.

It is also important to note that the construction and arrangement of the elements of the present disclosure as shown in the exemplary embodiments is illustrative only. Although only a few embodiments of the present innovations have been described in detail in this disclosure, those skilled in the art who review this disclosure will readily appreciate that, unless otherwise described, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating positions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present invention, and further it is to be understood that such concepts are intended to be covered by the following claims unless these claims by their language expressly state otherwise.

The invention claimed is:

1. A surgical bone plate and caddy assembly comprising:
a) a bone plate comprising first and second, spaced apart segments connected by a middle portion, wherein each of the first and second segments comprises a top surface, a bottom surface, an indented section, and first and second bone plate fastener apertures, wherein in each of the first and second segments the indented section is between the first and second bone plate fastener apertures of said segment and has a first peripheral edge, a second peripheral edge, and a width extending across the indented section from the first peripheral edge to the second peripheral edge;
b) a caddy connected to the first and second peripheral edges of the indented section of the first segment of the bone plate, wherein the caddy comprises:
i) a first body comprising a shell portion, an elastomeric portion held by the shell portion, and a first caddy fastener aperture formed in the elastomeric portion of the first body, wherein the first caddy fastener aperture extends from a top fastener opening to a bottom fastener opening, wherein the first caddy fastener aperture includes an interior surface, wherein a plurality of deflectable ribs are formed on the interior surface of the first caddy fastener aperture, and wherein the first caddy fastener aperture is aligned with the first bone plate fastener aperture of the first segment of the bone plate;
ii) a second body comprising a shell portion, an elastomeric portion held by the shell portion, and a second caddy fastener aperture formed in the elastomeric portion of the second body, wherein the second caddy fastener aperture extends from a top fastener opening to a bottom fastener opening, wherein the second caddy fastener aperture includes an interior surface, wherein a plurality of deflectable ribs are formed on the interior surface of the second caddy fastener aperture, and wherein the second caddy fastener aperture is aligned with the second bone plate fastener aperture of the first segment of the bone plate;
iii) a central portion located between the first and second bodies such that a gap is formed between the first and second bodies above the central portion, wherein the central portion is connected to the first and second peripheral edges of the indented section of the first segment of the bone plate such that the central portion removably connects the caddy to the first segment at first and second connections across the width of the indented section between the first and second bodies and between the first and second bone plate fastener apertures of the first segment;
c) a first fastener inserted into and held in the first caddy fastener aperture of the first body in a manner such that the ribs on the interior surface of the first caddy fastener aperture hold the first fastener and deflect as the first fastener is advanced through the first caddy fastener aperture into the aligned first bone plate fastener aperture in a direction from the top fastener opening toward the bottom fastener opening of the first caddy fastener aperture; and
d) a second fastener inserted into and held in the second caddy fastener aperture of the second body in a manner such that the ribs on the interior surface of the second caddy fastener aperture hold the second fastener and deflect as the second fastener is advanced through the second caddy fastener aperture into the aligned second bone plate fastener aperture in a direction from the top fastener opening toward the bottom fastener opening of the second caddy fastener aperture.

2. The surgical plate and caddy assembly of claim 1, wherein:
the central portion further comprises first and second clip portions that respectively connect the central portion to the first and second peripheral edges of the indented section of the first segment of the bone plate, and
both of said first and second clip portions deflect to remove the caddy from the bone plate.

3. The surgical plate and caddy assembly of claim 1, wherein:
each fastener of the first and second fasteners includes a head, and wherein each of said first and second caddy fastener apertures includes a rim, wherein the rim of the first caddy fastener aperture engages the head of the first fastener and wherein the rim of the second caddy fastener aperture engages the head of the second fastener.

4. The surgical plate and caddy assembly of claim 1, wherein:
the shell portion of the first body is made from a harder material than the elastomeric portion of the first body and the shell portion of the second body is made from a harder material than the elastomeric portion of the second body.

5. The surgical plate and caddy assembly of claim 4, wherein said shell portion and elastomeric portion of each of the first and second bodies are molded together.

6. The surgical bone plate and caddy assembly of claim 1, wherein the plurality of deflectable ribs on the interior surface of each of the first and second caddy fastener apertures extend vertically.

7. The surgical bone plate and caddy assembly of claim 1, wherein each of the elastomeric portions of the first and second caddy bodies comprises a thermoplastic elastomer.

8. The surgical bone plate and caddy assembly of claim 1, wherein each of the plurality of first and second fasteners comprises a threaded shank and a threaded head.

9. The combination of claim 8, wherein the threaded head of each of the fasteners is tapered.

10. The surgical bone plate and caddy assembly of claim 1, wherein each of the shell portions comprises an acrylonitrile butadiene styrene polymer.

11. The surgical bone plate and caddy assembly of claim 1, wherein the central portion includes an aperture.

12. The surgical bone plate and caddy assembly of claim 1, further comprising an additional caddy connected to the first and second peripheral edges of the indented section of the second segment of the bone plate, wherein the additional caddy comprises:
   i) a first body comprising a shell portion, an elastomeric portion held by the shell portion, and a first caddy fastener aperture formed in the elastomeric portion of the first body of the additional caddy, wherein the first caddy fastener aperture of the additional caddy extends from a top fastener opening to a bottom fastener opening, wherein the first caddy fastener aperture of the additional caddy includes an interior surface, wherein a plurality of deflectable ribs are formed on the interior surface of the first caddy fastener aperture of the additional caddy, and wherein the first caddy fastener aperture of the additional caddy is aligned with the first bone plate fastener aperture of the second bone plate segment;
   ii) a second body comprising a shell portion, an elastomeric portion held by the shell portion, and a second caddy fastener aperture formed in the elastomeric portion of the second body of the additional caddy, wherein the second caddy fastener aperture of the additional caddy extends from a top fastener opening to a bottom fastener opening, wherein the second caddy fastener aperture of the additional caddy includes an interior surface, wherein a plurality of deflectable ribs are formed on the interior surface of the second caddy fastener aperture of the additional caddy, and wherein the second caddy fastener aperture of the additional caddy is aligned with the second bone plate fastener aperture of the second bone plate segment; and
   iii) a central portion located between the first and second bodies of the additional caddy such that a gap is formed between the first and second bodies of the additional caddy above the central portion of the additional caddy, wherein the central portion of the additional caddy is connected to the first and second peripheral edges of the indented section of the first bone plate segment such that the central portion of the additional caddy removably connects the additional caddy to the second bone plate segment at first and second connections across the width of the indented section of the second bone plate segment between the first and second bodies of the additional caddy and between the first and second bone plate fastener apertures of the second bone plate segment.

13. The surgical bone plate and caddy assembly of claim 12, further comprising:
   a) a third fastener inserted into and held in the first caddy fastener aperture of the first body of the additional caddy in a manner such that the ribs on the interior surface of the first caddy fastener aperture of the additional caddy hold the third fastener and deflect as the third fastener is advanced through the first caddy fastener aperture of the additional caddy into the aligned first bone plate fastener aperture of the second segment in a direction from the top fastener opening toward the bottom fastener opening of the first caddy fastener aperture of the additional caddy; and
   b) a fourth fastener inserted into and held in the second caddy fastener aperture of the second body of the additional caddy in a manner such that the ribs on the interior surface of the second caddy fastener aperture of the additional caddy hold the fourth fastener and deflect as the fourth fastener is advanced through the second caddy fastener aperture of the additional caddy into the aligned second bone plate fastener aperture of the second segment in a direction from the top fastener opening toward the bottom fastener opening of the second caddy fastener aperture of the additional caddy.

14. The surgical bone plate and caddy assembly of claim 1, wherein the bottom fastener openings of each of the first and second bodies is larger than the top fastener openings, respectively, of each of the first and second bodies.

15. A method of installing fasteners into a bone plate, the method comprising the steps of:
   a) providing the bone plate, said bone plate comprising first and second, spaced apart segments connected by a middle portion, wherein each of the first and second segments comprises a top surface, a bottom surface, an indented section, and first and second bone plate fastener apertures, wherein in each of the first and second segments the indented section is between the first and second bone plate fastener apertures of said segment and has a first peripheral edge, a second peripheral edge, and a width extending across the indented section from the first peripheral edge to the second peripheral edge;
   b) providing a caddy, said caddy comprising:
      i) a first body comprising a shell portion, an elastomeric portion held by the shell portion, and a first caddy fastener aperture formed in the elastomeric portion of the first body, wherein the first caddy fastener aperture extends from a top fastener opening to a bottom fastener opening, wherein the first caddy fastener aperture includes an interior surface, and wherein a plurality of deflectable ribs are formed on the interior surface of the first caddy fastener aperture;
      ii) a second body comprising a shell portion, an elastomeric portion held by the shell portion, and a second caddy fastener aperture formed in the elastomeric portion of the second body, wherein the second caddy fastener aperture extends from a top fastener opening to a bottom fastener opening, wherein the second caddy fastener aperture includes an interior surface, and wherein a plurality of deflectable ribs are formed on the interior surface of the second caddy fastener aperture;

iii) a central portion located between the first and second bodies such that a gap is formed between the first and second bodies above the central portion;
iv) a first fastener held in the first caddy fastener aperture, wherein the ribs on the interior surface of the first caddy fastener aperture hold the first fastener; and
v) a second fastener held in the second caddy fastener aperture, wherein the ribs on the interior surface of the second caddy fastener aperture hold the second fastener;

c) connecting the central portion of the caddy to the first and second peripheral edges of the indented section of the first segment of the bone plate such that the first caddy fastener aperture is aligned with the first bone plate fastener aperture of the first segment of the bone plate and the second caddy fastener aperture is aligned with the second bone fastener plate aperture of the first segment of the bone plate and such that the central portion removably connects the caddy to the first segment of the bone plate at first and second connections across the width of the indented section of the first segment of the bone plate between the first and second bodies of the caddy and between the first and second bone plate fastener apertures of the first segment of the bone plate;

d) while the central portion of the caddy connects the caddy to the first segment of the bone plate, advancing each of the first and second fastener through bottom openings of the first and second bone plate fastener apertures, respectively, to secure the bone plate to a bone, wherein the ribs on the interior surface of the first caddy fastener aperture deflect as the first fastener is advanced, and wherein the ribs on the interior surface of the second caddy fastener aperture deflect as the second fastener is advanced; and e) removing the caddy from the bone plate.

16. The method of installing fasteners into a bone plate of claim 15, wherein the caddy is flexible, and wherein the removing step comprises flexing the flexible caddy.

17. The method of installing fasteners into a bone plate of claim 15, further comprising the steps of:
a) providing an additional caddy comprising:
i) a first body comprising a shell portion, an elastomeric portion held by the shell portion, and a first caddy fastener aperture formed in the elastomeric portion of the first body of the additional caddy, wherein the first caddy fastener aperture of the additional caddy extends from a top fastener opening to a bottom fastener opening, wherein the first caddy fastener aperture of the additional caddy includes an interior surface, and wherein a plurality of deflectable ribs are formed on the interior surface of the first caddy fastener aperture of the additional caddy;
ii) a second body comprising a shell portion, an elastomeric portion held by the shell portion, and a second caddy fastener aperture formed in the elastomeric portion of the second body of the additional caddy, wherein the second caddy fastener aperture of the additional caddy extends from a top fastener opening to a bottom fastener opening, wherein the second caddy fastener aperture of the additional caddy includes an interior surface, and wherein a plurality of deflectable ribs are formed on the interior surface of the second caddy fastener aperture of the additional caddy;

iii) a central portion located between the first and second bodies of the additional caddy such that a gap is formed between the first and second bodies of the additional caddy above the central portion of the additional caddy;
iv) a third fastener held in the first caddy fastener aperture of the additional caddy, wherein the ribs on the interior surface of the first caddy fastener aperture of the additional caddy hold the third fastener; and
v) a fourth fastener held in the second caddy fastener aperture of the additional caddy, wherein the ribs on the interior surface of the second caddy fastener aperture of the additional caddy hold the fourth fastener;

b) connecting the central portion of the additional caddy to the first and second peripheral edges of the indented section of the second segment of the bone plate such that the first caddy fastener aperture of the additional caddy is aligned with the first bone plate fastener aperture of the second segment of the bone plate and the second caddy fastener aperture of the additional caddy is aligned with the second bone fastener plate aperture of the second segment of the bone plate and such that the central portion of the additional caddy removably connects the caddy to the second segment of the bone plate at first and second connections across the width of the indented section of the second segment of the bone plate between the first and second bodies of the additional caddy and between the first and second bone plate fastener apertures of the second segment of the bone plate;

c) while the central portion of the additional caddy connects the additional caddy to the second segment of the bone plate, advancing each of the first and second fastener through bottom openings of the first and second bone plate fastener apertures of the additional caddy, respectively, to secure the bone plate to a bone, wherein the ribs on the interior surface of the first caddy fastener aperture of the additional caddy deflect as the third fastener is advanced, and wherein the ribs on the interior surface of the second caddy fastener aperture of the additional caddy deflect as the fourth fastener is advanced; and d) removing the additional caddy from the bone plate.

18. The method of claim 15, wherein the bottom fastener openings of each of the first and second bodies is larger than the top fastener openings, respectively, of each of the first and second bodies.

19. A surgical fastener caddy guide that is configured to be removably connected to a bone plate comprising first and second bone plate fastener apertures, said caddy comprising:
a) a first body comprising a shell portion, an elastomeric portion held by the shell portion, and a first caddy fastener aperture formed in the elastomeric portion of the first body, wherein the first caddy fastener aperture extends from a top fastener opening to a bottom fastener opening, wherein the first caddy fastener aperture includes an interior surface, wherein a plurality of deflectable ribs are formed on the interior surface of the first caddy fastener aperture, and wherein the first caddy fastener aperture is aligned with the first bone plate fastener aperture when the fastener caddy guide is connected to the bone plate;
b) a second body comprising a shell portion, an elastomeric portion held by the shell portion, and a second caddy fastener aperture formed in the elastomeric portion of the second body, wherein the second caddy fastener aperture extends from a top fastener opening to a bottom fastener opening, wherein the second caddy fastener aperture includes an interior surface, wherein a plurality of deflectable ribs are formed on the interior surface of the second caddy fastener aperture, and wherein the second caddy fastener aperture is aligned with the second bone plate aperture when the fastener caddy guide is connected to the bone plate;

c) a central portion located between the first and second bodies such that a gap is formed between the first and second bodies above the central portion, wherein the central portion includes a first clip portion that removably couples the caddy to a first peripheral edge of the bone plate at a first connection between the first and second bodies and a second clip portion that removably couples the caddy to a second peripheral edge of the bone plate at a second connection between the first and second bodies.

20. The surgical fastener caddy guide of claim 19, wherein said plurality of deflectable ribs of said first and second caddy fastener apertures of the first and second caddy bodies are angled.

21. Fastener caddy guide of claim 19, wherein the bottom fastener openings of each of the first and second bodies is larger than the top fastener openings, respectively, of each of the first and second bodies.

22. A method of assembling a surgical bone plate and fastener caddy, the method comprising the steps of:
a) providing the bone plate, said bone plate comprising first and second, spaced apart segments connected by a middle portion, wherein each of the first and second segments comprises a top surface, a bottom surface, an indented section, and first and second bone plate fastener apertures, wherein in each of the first and second segments the indented section is between the first and second bone plate fastener apertures of said segment and has a first peripheral edge, a second peripheral edge, and a width extending across the indented section from the first peripheral edge to the second peripheral edge;
b) providing the fastener caddy, said caddy comprising:
  i) a first body comprising a shell portion, an elastomeric portion held by the shell portion, and a first caddy fastener aperture formed in the elastomeric portion of the first body, wherein the first caddy fastener aperture extends from a top fastener opening to a bottom fastener opening, wherein the first caddy fastener aperture includes an interior surface, and wherein a plurality of deflectable ribs are formed on the interior surface of the first caddy fastener aperture;
  ii) a second body comprising a shell portion, an elastomeric portion held by the shell portion, and a second caddy fastener aperture formed in the elastomeric portion of the second body, wherein the second caddy fastener aperture extends from a top fastener opening to a bottom fastener opening, wherein the second caddy fastener aperture includes an interior surface, and wherein a plurality of deflectable ribs are formed on the interior surface of the second caddy fastener aperture; and
  iii) a central portion located between the first and second bodies such that a gap is formed between the first and second bodies above the central portion; and
c) connecting the central portion of the caddy to the first and second peripheral edges of the indented section of the first bone plate segment such that the first caddy fastener aperture is aligned with the first bone plate fastener aperture of the first bone plate segment and the second caddy fastener aperture is aligned with the second bone fastener plate aperture of the first bone plate segment and such that the central portion removably connects the caddy to the first bone plate segment at first and second connections across the width of the indented section of the bone plate segment between the first and second bodies of the caddy and between the first and second bone plate fastener apertures of the first bone plate segment.

23. The method of claim 22, wherein the bottom fastener openings of each of the first and second bodies is larger than the top fastener openings, respectively, of each of the first and second bodies.

* * * * *

UNITED STATES PATENT AND TRADEMARK OFFICE
CERTIFICATE OF CORRECTION

PATENT NO. : 11,957,394 B2
APPLICATION NO. : 17/114566
DATED : April 16, 2024
INVENTOR(S) : Didyk et al.

Page 1 of 1

It is certified that error appears in the above-identified patent and that said Letters Patent is hereby corrected as shown below:

On the Title Page

(71) Applicant:
"J.M. LONGYEAR MANUFACTURING, LLC," should be -- J.M. Longyear Manufacturing, LLC, dba Able Medical Devices --

(73) Assignee:
"J.M. LONGYEAR MANUFACTURING, LLC," should be -- J.M. Longyear Manufacturing, LLC, dba Able Medical Devices --

In the Claims

Column 16, Claim 17, Line 35:
"the bone plate, advancing each of the first and second" should be -- the bone plate, advancing each of the third and fourth --

Signed and Sealed this
Fourteenth Day of May, 2024

Katherine Kelly Vidal
*Director of the United States Patent and Trademark Office*